US 7,814,901 B2

(12) United States Patent
Lieberman et al.

(10) Patent No.: US 7,814,901 B2
(45) Date of Patent: Oct. 19, 2010

(54) NEBULIZING DRUG DELIVERY DEVICE WITH INCREASED FLOW RATE

(75) Inventors: Eric A. Lieberman, Scotch Plains, NJ (US); Dirk Von Hollen, Clark, NJ (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 11/367,649

(22) Filed: Mar. 3, 2006

(65) Prior Publication Data
US 2006/0201502 A1    Sep. 14, 2006

Related U.S. Application Data

(60) Provisional application No. 60/659,919, filed on Mar. 9, 2005.

(51) Int. Cl.
*A61M 11/00*  (2006.01)

(52) U.S. Cl. .................. 128/200.16; 239/102.1

(58) Field of Classification Search ........... 128/200.14, 128/200.16, 200.18; 239/102.1, 4, 102.2, 239/338, 8, 3, 13; 264/5, 7, 9, 10, 82, 22, 264/23, 24, 13; 209/8, 214, 128, 129, 130; 310/317, 316, 318, 319; 261/DIG. 48, 78
See application file for complete search history.

(56) References Cited

U.S. PATENT DOCUMENTS

| 2,027,298 A | 1/1936 | Wheat |
| 2,228,009 A | 1/1941 | Harford |
| 2,659,042 A | 11/1953 | Anderson et al. |
| 3,274,476 A | 9/1966 | Wildum |
| 3,387,607 A * | 6/1968 | Gauthier et al. ........ 128/200.16 |
| 3,472,455 A | 10/1969 | Johnson et al. |
| 3,490,697 A * | 1/1970 | Best, Jr. .................. 239/102.2 |
| 3,828,201 A | 8/1974 | Allen, Sr. |
| 3,918,641 A * | 11/1975 | Lehmann et al. ............ 118/620 |
| 3,919,615 A | 11/1975 | Niecke |
| 4,200,093 A * | 4/1980 | Camp .................... 128/200.14 |
| 4,244,361 A | 1/1981 | Neubert |
| 4,667,141 A | 5/1987 | Steele |
| 4,714,078 A | 12/1987 | Paluch |
| 4,820,453 A | 4/1989 | Huang |
| 4,902,955 A | 2/1990 | Manis et al. |
| 4,951,661 A | 8/1990 | Sladek |
| 4,976,259 A | 12/1990 | Higson et al. |
| 5,062,419 A | 11/1991 | Rider |
| 5,214,368 A | 5/1993 | Wells |
| 5,277,175 A | 1/1994 | Riggs et al. |
| 5,485,827 A * | 1/1996 | Zapol et al. ............ 128/200.14 |

(Continued)

FOREIGN PATENT DOCUMENTS

AU    2003254386 B2    3/2004

(Continued)

*Primary Examiner*—Steven O Douglas
(74) *Attorney, Agent, or Firm*—Timothy A. Nathan

(57) ABSTRACT

The present invention provides a nebulizing drug delivery system for delivering an aerosolized drug to a user having various features to increase the capacity of the drug delivery device. The drug delivery system includes a heater to increase the viscosity of the drug, a double aerosolizing system to double the capacity of the device, and a valve system to continuously replenish drug to the aerosol generator thereby providing a high speed delivery.

14 Claims, 16 Drawing Sheets

U.S. PATENT DOCUMENTS

Figure 1:
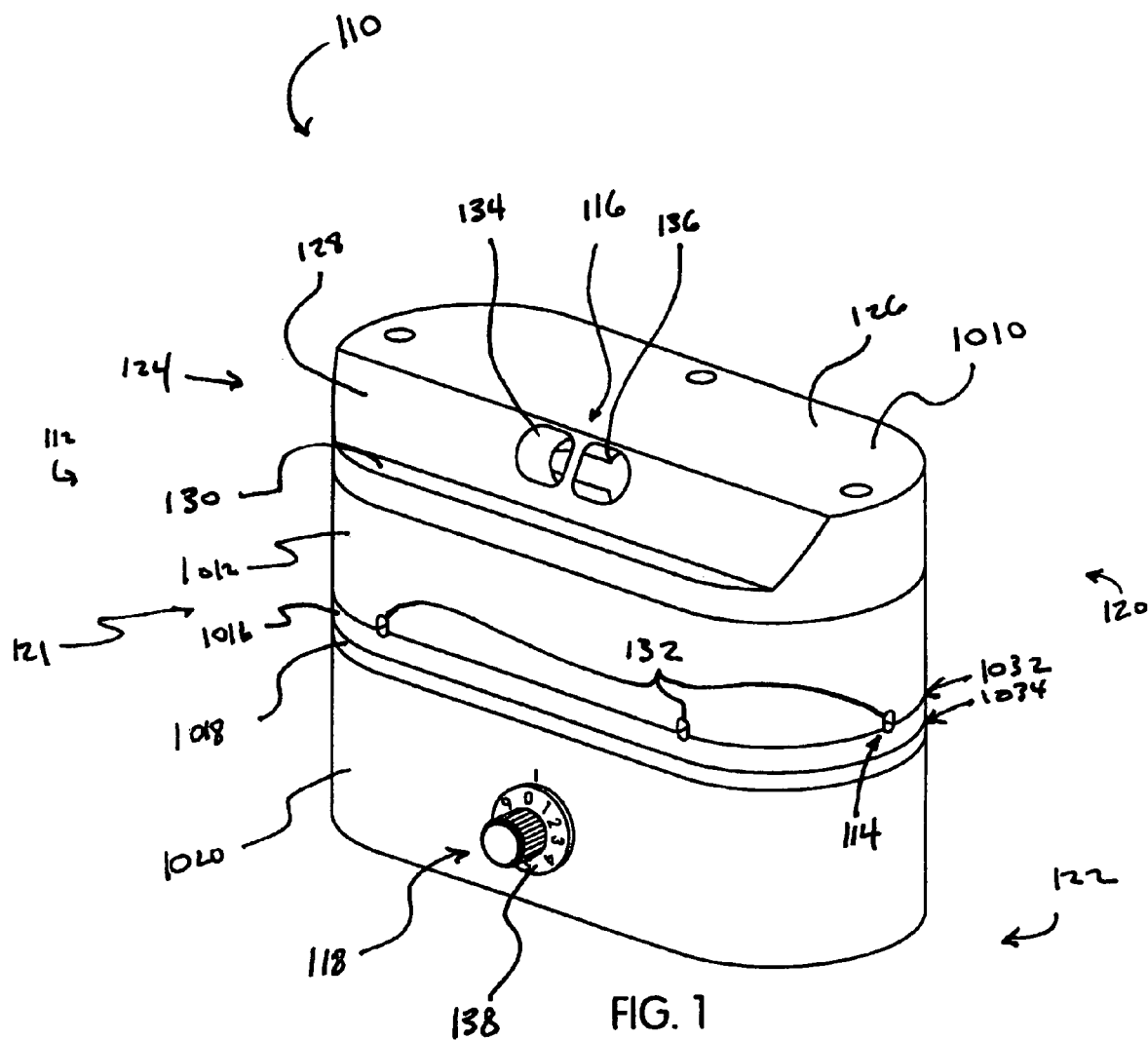

| | | | |
|---|---|---|---|
| 5,687,715 | A | 11/1997 | Landis et al. |
| 5,707,352 | A * | 1/1998 | Sekins et al. ............... 604/509 |
| 5,724,965 | A | 3/1998 | Handke et al. |
| 5,865,171 | A * | 2/1999 | Cinquin ............... 128/203.12 |
| 5,908,158 | A | 6/1999 | Cheiman |
| 6,007,940 | A | 12/1999 | Spotnitz |
| 6,106,971 | A | 8/2000 | Spotnitz |
| 6,152,383 | A | 11/2000 | Chen |
| 6,202,642 | B1 | 3/2001 | McKinnon et al. |
| 6,234,167 | B1 * | 5/2001 | Cox et al. ............... 128/200.14 |
| 6,241,162 | B1 | 6/2001 | Takahashi et al. |
| 6,283,118 | B1 | 9/2001 | Lu |
| 6,328,030 | B1 | 12/2001 | Kidwell et al. |
| 6,357,671 | B1 | 3/2002 | Cewers |
| 6,379,616 | B1 | 4/2002 | Sheiman |
| 6,402,046 | B1 | 6/2002 | Loser |
| 6,443,146 | B1 | 9/2002 | Voges |
| 6,478,754 | B1 | 11/2002 | Babaev |
| 6,490,186 | B2 | 12/2002 | Cho |
| 6,501,197 | B1 | 12/2002 | Cornog et al. |
| 6,516,802 | B2 | 2/2003 | Hansen et al. |
| 6,530,370 | B1 | 3/2003 | Heinonen |
| 6,530,570 | B2 | 3/2003 | Ku |
| 6,550,476 | B1 | 4/2003 | Ryder |
| 6,640,804 | B2 | 11/2003 | Ivri et al. |
| 6,727,446 | B1 | 4/2004 | Mayo et al. |
| 6,854,465 | B2 | 2/2005 | Bordewick et al. |
| 7,037,306 | B2 | 5/2006 | Podany |
| 7,089,941 | B2 | 8/2006 | Bordewick et al. |
| 7,179,254 | B2 | 2/2007 | Pendekanti |
| 2002/0011248 | A1 | 1/2002 | Hansen et al. |
| 2002/0082666 | A1 | 6/2002 | Babaev |
| 2003/0205229 | A1 | 11/2003 | Crockford et al. |
| 2004/0025882 | A1 | 2/2004 | Madaus et al. |
| 2004/0267167 | A1 | 12/2004 | Podany |
| 2005/0010202 | A1 | 1/2005 | Podany |
| 2005/0042170 | A1 * | 2/2005 | Jiang et al. ............... 424/45 |
| 2005/0215942 | A1 | 9/2005 | Abrahamson |
| 2006/0151624 | A1 * | 7/2006 | Grundler et al. ............... 237/67 |
| 2006/0163641 | A1 | 7/2006 | Okumura |
| 2006/0243274 | A1 * | 11/2006 | Lieberman et al. ..... 128/200.14 |

FOREIGN PATENT DOCUMENTS

| | | |
|---|---|---|
| AU | 2006252145 B2 | 1/2007 |
| RU | 2070062 | 12/1996 |
| RU | 2076746 | 4/1997 |
| WO | WO95/26236 A1 | 10/1995 |
| WO | WO 2004/017848 | 3/2004 |

* cited by examiner

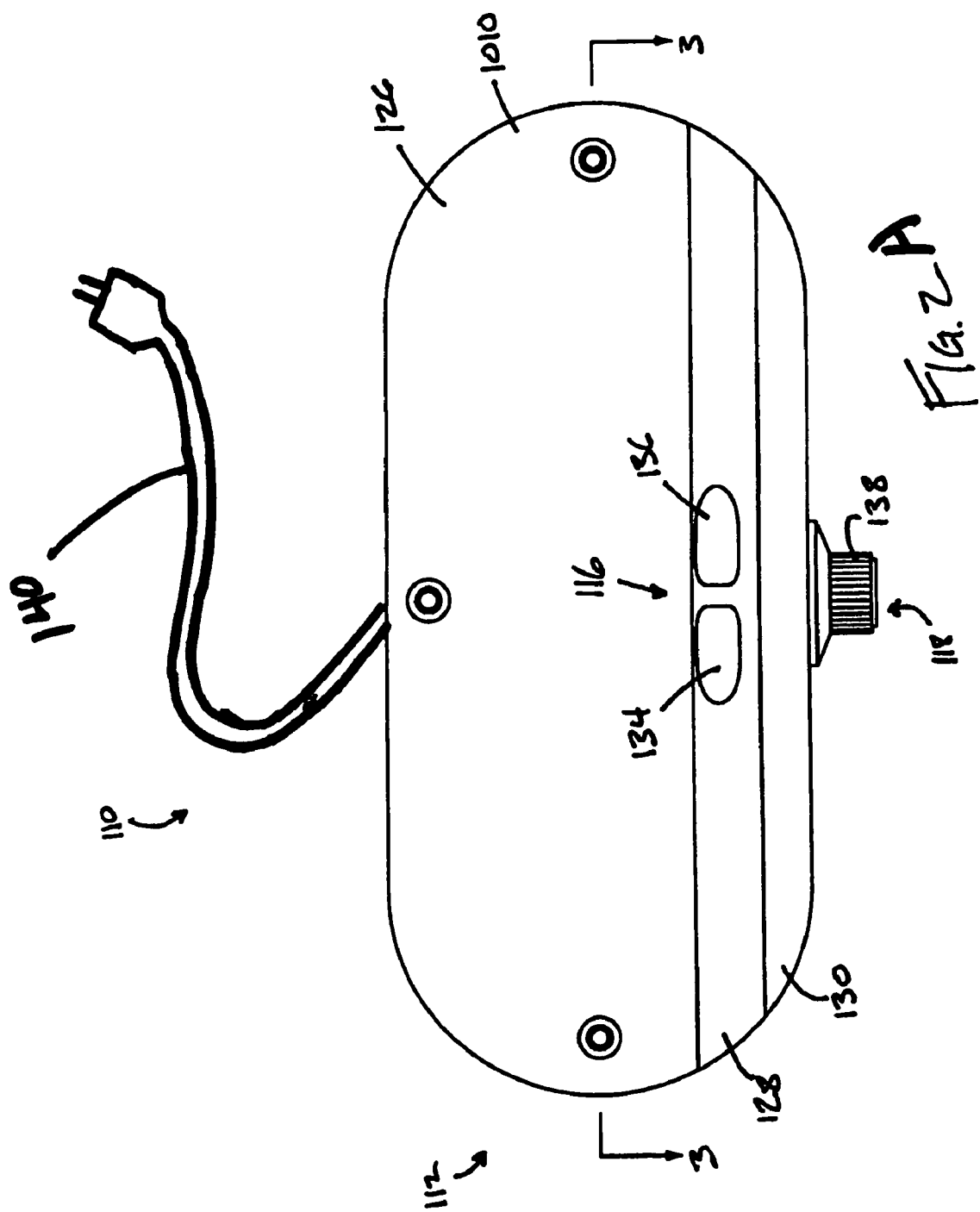

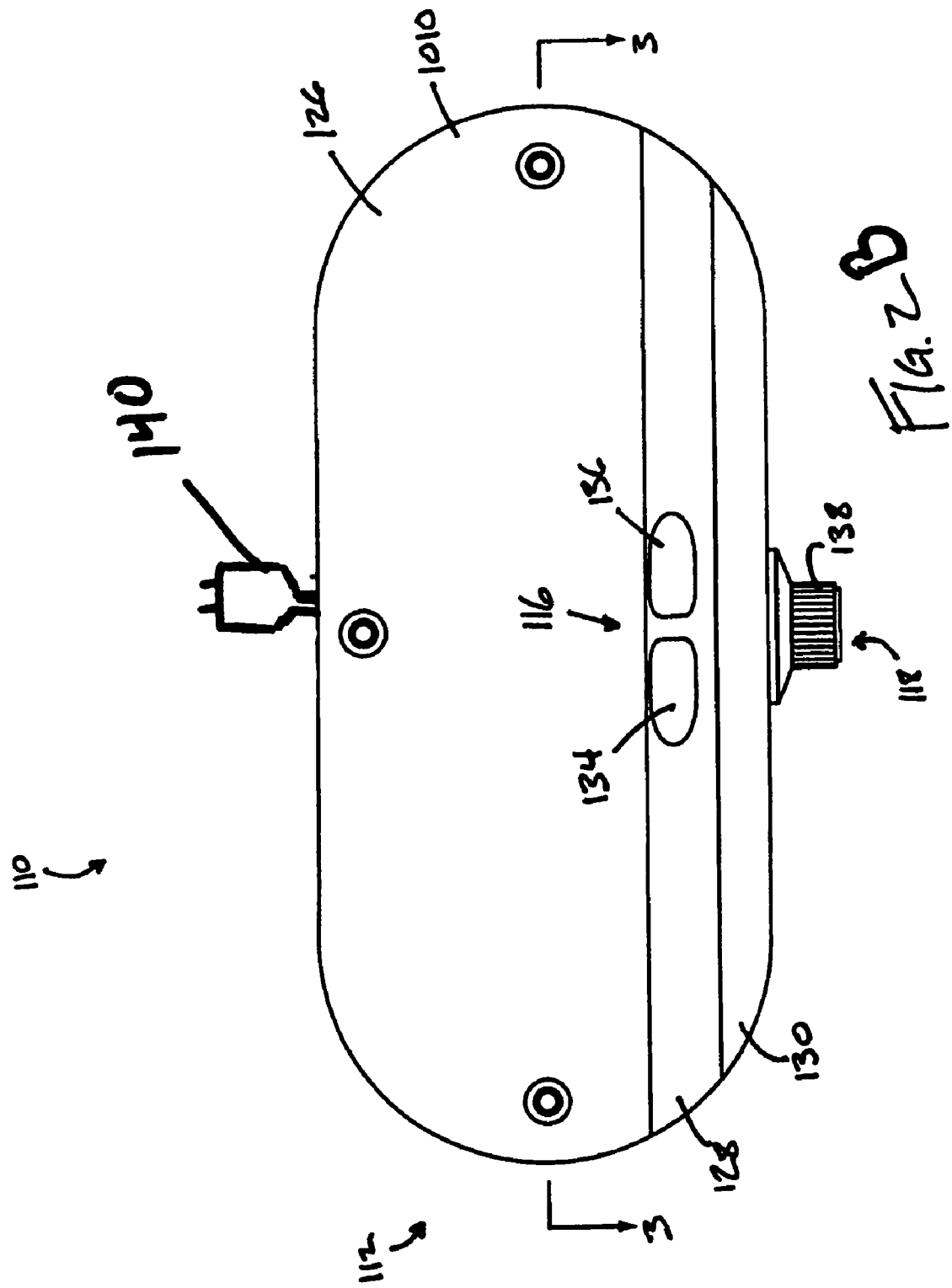

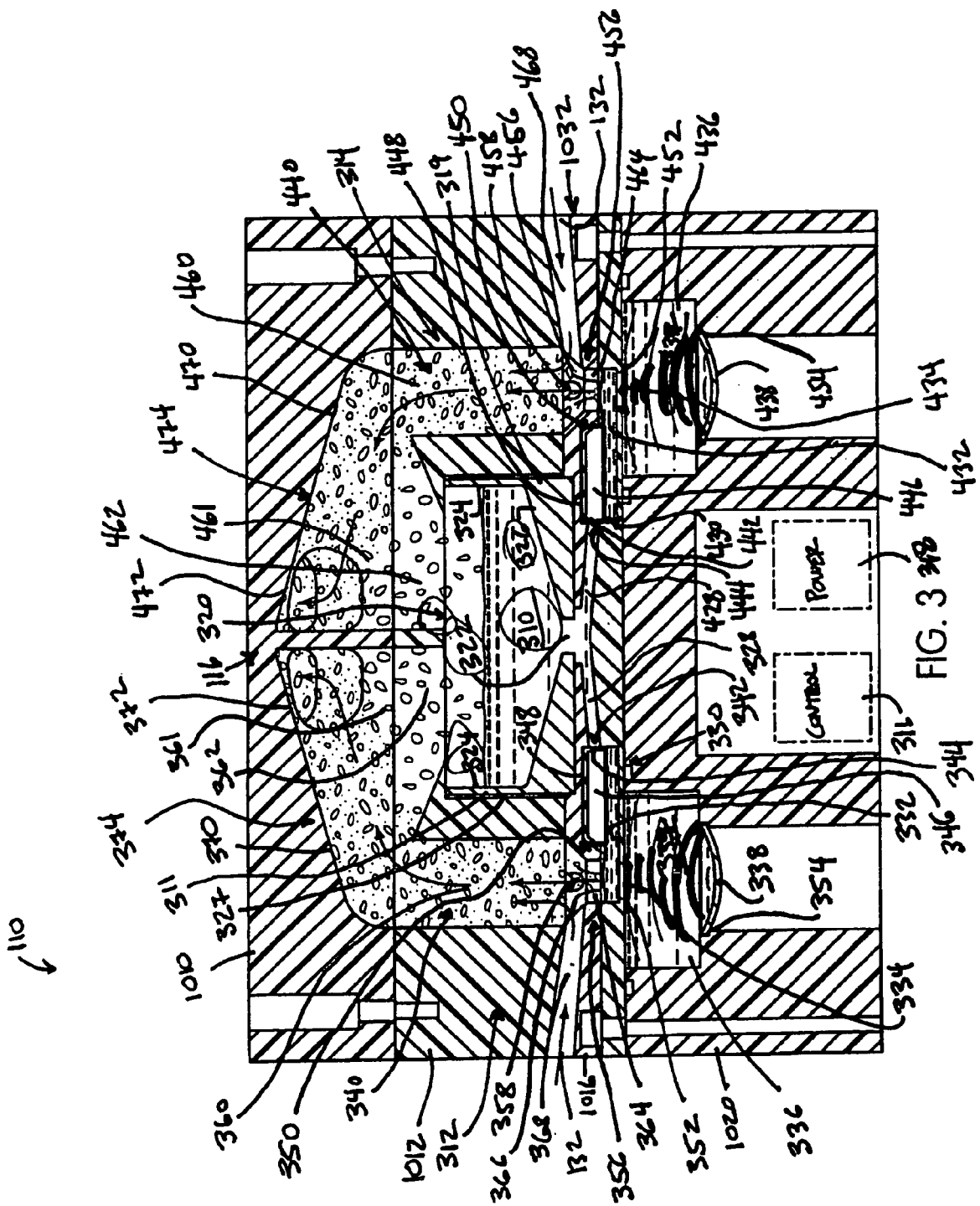

```
                    ┌─────────────────┐
          910       │   POWER ON      │──912
            ↘       └─────────────────┘
                            ↓
                    ┌─────────────────┐
          914 ──────│ TEMPERATURE SET │
                    │ TO DESIRED LEVEL│
                    └─────────────────┘
                            ↓
                    ┌─────────────────┐
          916 ──────│    HEATER       │←──────────────┐
                    │ HEATS RESERVOIR │←──────┐       │
                    └─────────────────┘       │       │
                            ↓                 │       │
          918 ──────    ◇ IS TEMPERATURE ◇  NO│       │
                        ACHIEVED?─────────────┘       │
                            │ YES                     │
                            ↓              920        │
                    ┌─────────────────┐               │
                    │  VALVE OPENS    │       926     │
                    └─────────────────┘    ┌────────────────┐
                            ↓              │ VALVE CLOSES   │
          922                              │ AND ACOUSTIC   │
                    ┌─────────────────┐    │ WAVE GENERATOR │
                    │                 │    │ IS DEACTIVATED │
                    │ ACOUSTIC WAVE   │    └────────────────┘
                    │ GENERATOR       │            ↑
                    │ IS ACTIVATED AND│            │
                    │ LIQUID IS       │            │
                    │ AEROSOLIZED     │            │
                    └─────────────────┘            │
                            ↓                      │
          ┌──────────┐                             │
          │ HEATER   │───→                   924   │
          │DEACTIVATES│──→ ◇ IS TEMPERATURE ◇ BELOW│
          └──────────┘ ABOVE MAINTAINED IN ────────┘
             ↑ 928         RESERVOIR?
             │                │ YES
          ┌────────┐          ↓           930
          │CONTINUE│       ◇ IS TREATMENT ◇ NO
          │TREATMENT│←─────  COMPLETE? ────┘
          └────────┘          │ YES
             ↑                ↓           932
                         ┌─────────────┐
                         │  POWER OFF  │
                         └─────────────┘
```

FIG. 10

NEBULIZING DRUG DELIVERY DEVICE WITH INCREASED FLOW RATE

CROSS-REFERENCE TO RELATED APPLICATIONS

This application claims priority under 35 U.S.C. § 119(e) from provisional U.S. Patent Application No. 60/659,919 filed Mar. 9, 2005 the contents of which are incorporated herein by reference.

BACKGROUND OF THE INVENTION

1. Field of the Invention

The present invention relates to drug delivery devices, and, in particular, to nebulizers used in an aerosolized drug delivery.

2. Description of the Related Art

Nebulizing drug delivery devices that use ultrasonic energy to nebulize a drug solution are generally known. Such devices typically include an acoustic wave generator to generate acoustic waves that are transmitted to a drug solution. The ultrasonic energy transmitted to the drug solution in the form of the acoustic waves energizes the drug solution such that nebulized particles of the drug solution are formed. The ultrasonic energy may be delivered with a maximum density at a focal point of the acoustic waves, and nebulization efficiency of the drug solution may be enhanced when an upper surface of a pool of the drug solution is located at or near the focal point of the acoustic waves. However, the ability to take advantage of enhanced nebulization efficiency in this manner has been limited by the fact that the upper surface of the drug solution lowers during nebulization as the amount of drug solution in the device is depleted.

It should be appreciated that several conventional nebulizing drug delivery devices are configured to deliver drug solutions to a user's lungs via inhalation. But these devices may not be capable of effectively or efficiently nebulizing various types of drug solutions for delivery that are typically delivered directly into a patient's lungs, such as through injection. Thus, typical nebulizing drug delivery devices may not be particularly effective or efficient in delivering drug solutions of a higher viscosity, and/or drug solutions that must be delivered at higher flow rates.

SUMMARY OF THE INVENTION

In accordance with the broad teachings of the invention, one aspect of the invention relates to a nebulizing device comprising a housing including an outlet and a drug reservoir for receiving a drug solution within the housing. An aerosol generator is disposed in communication with a fluid, and a barrier separates the fluid from a portion of the drug solution residing on the barrier. The barrier is capable of transmitting acoustic waves in the fluid to the portion of drug solution residing thereon. The acoustic waves in the drug solution operate to form nebulized particles from the portion of drug solution residing on the barrier to enable nebulized particles of the drug solution to be communicated to a user through the outlet. A valve permits drug solution within the reservoir to replenish the portion of drug solution residing on the barrier when the portion is less than a threshold amount.

In one embodiment, the valve comprises a float that floats on the portion of drug solution residing on the barrier, the float substantially sealing the reservoir from the barrier when the amount of drug solution residing on the barrier is above the threshold amount. The float permitting drug solution to flow from the reservoir to the barrier when the amount of drug solution residing on the barrier is less than the threshold amount.

In another aspect the invention relates to a nebulizing device comprising a housing having an inlet and an outlet, and a plurality of aerosol generators in communication with a fluid. A barrier is disposed between the fluid and a drug solution provided within the housing, the barrier being capable of transmitting acoustic waves in the fluid to the drug solution. The plurality of aerosol generators form a corresponding plurality of fountains that generate nebulized particles of the drug solution. The plurality of fountains are in communication with the outlet to enable a user to inhale nebulized particles of the drug solution from the plurality of aerosol regions through the outlet.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

A specific embodiment of the invention is now described with reference to the accompanying drawings, wherein:

FIG. 1 illustrates a perspective view of the nebulizing device in accordance with an embodiment of the invention.

FIG. 2A is a top plan view of an embodiment of the nebulizing device with a fixed length cord.

FIG. 2B is a top plan view of an embodiment of the nebulizing device with a cord in a retracted position.

FIG. 3 is a cross sectional view of the nebulizing device of FIG. 2A, taken along section line 3-3 of FIG. 2A, according to an embodiment of the invention.

FIG. 4 is a sectional view of the nebulizing device similar to FIG. 3, but illustrating the device with the valves between the barrier chambers and the drug reservoir open.

FIG. 5 is an exploded perspective view of the nebulizing drug delivery device, in accordance with one embodiment of the invention.

FIG. 6 is a cross-sectional view of the nebulizing device similar to FIG. 3, but including an alternative valve arrangement between the barrier chambers and the drug reservoir.

FIG. 7 is a cross-sectional view of the nebulizing device similar to FIG. 4, but including a solenoid to operate a valve for opening and closing the drug reservoir.

FIG. 8 is a cross-sectional view of the nebulizing device similar to FIG. 7, but illustrating the valve for opening and closing the drug reservoir as being open.

FIG. 9 is an exemplary illustration of the circuitry of the nebulizing device according to one embodiment of the invention.

FIG. 10 is an exemplary illustration of a method of controlling the nebulizing device in accordance with an embodiment of the invention.

FIGS. 11A-11C illustrate a front perspective view, a side plan view, and a rear plan view of the nebulizing drug delivery device, according to one embodiment of the invention.

FIG. 12 is a sectional view of the nebulizing device of FIG. 11B, taken along section line 12-12 of FIG. 11B, in accordance with an embodiment of the invention.

Figure 11A:
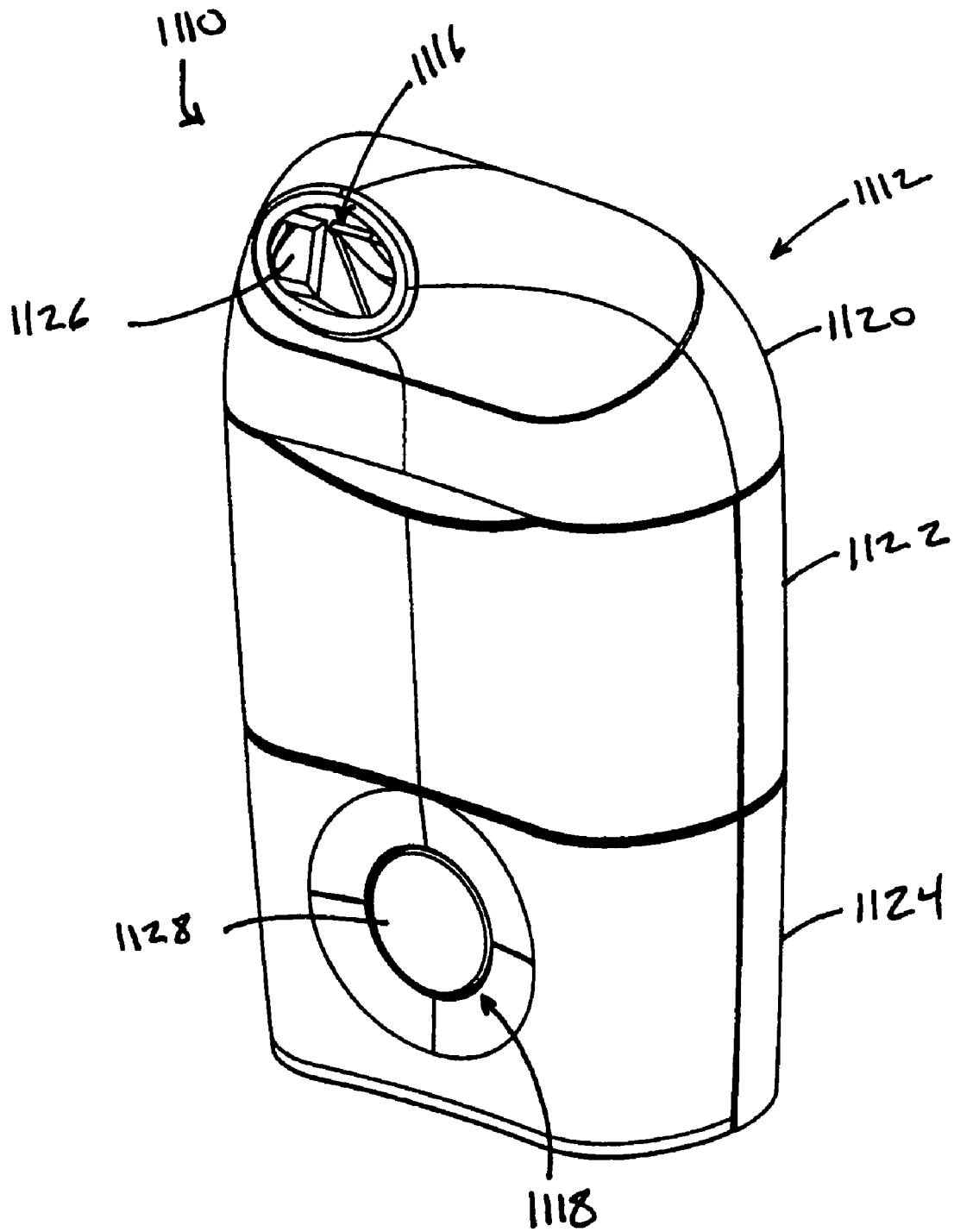
Figure 11B:
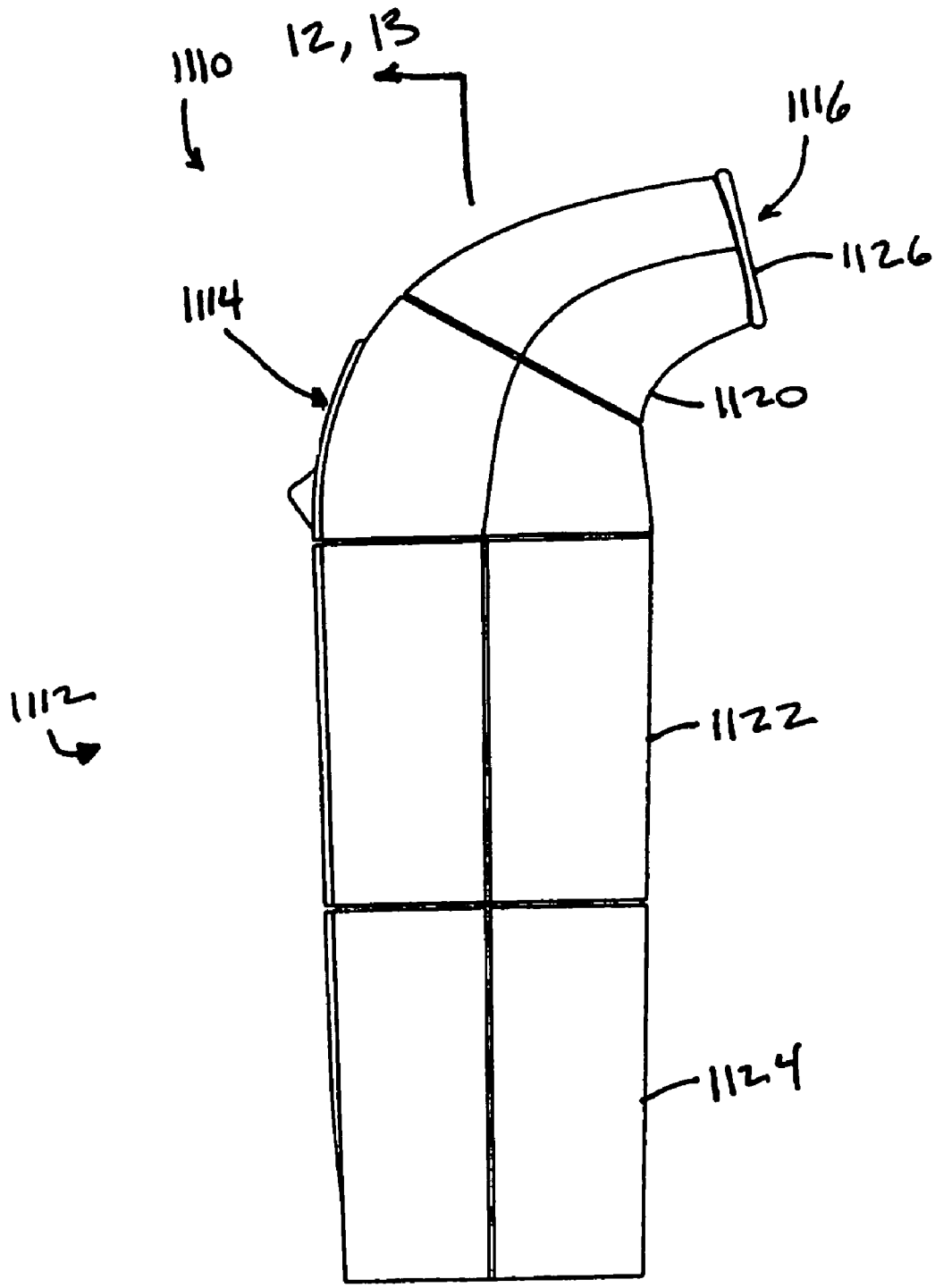
Figure 11C:
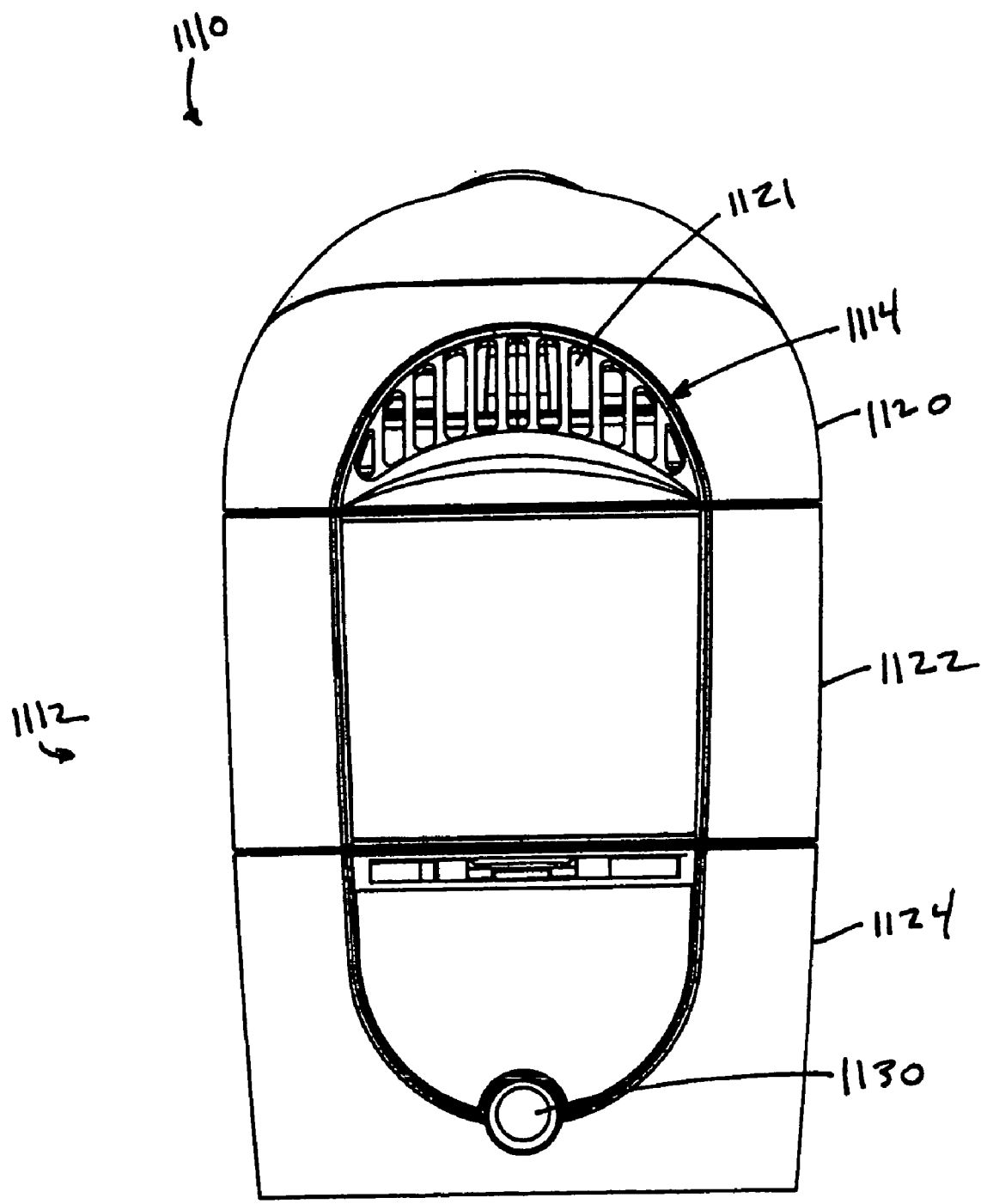
Figure 12:
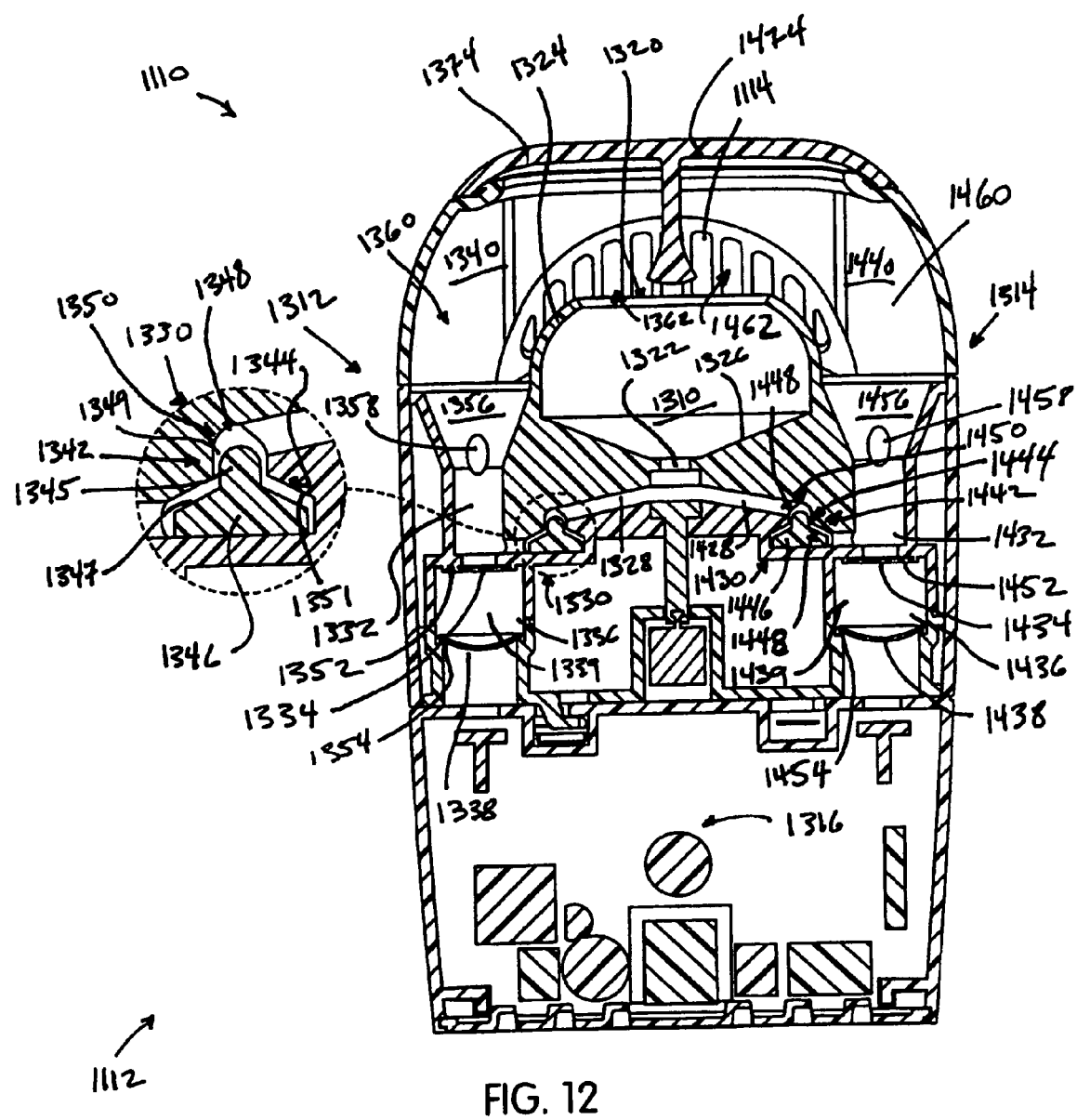
Figure 13:
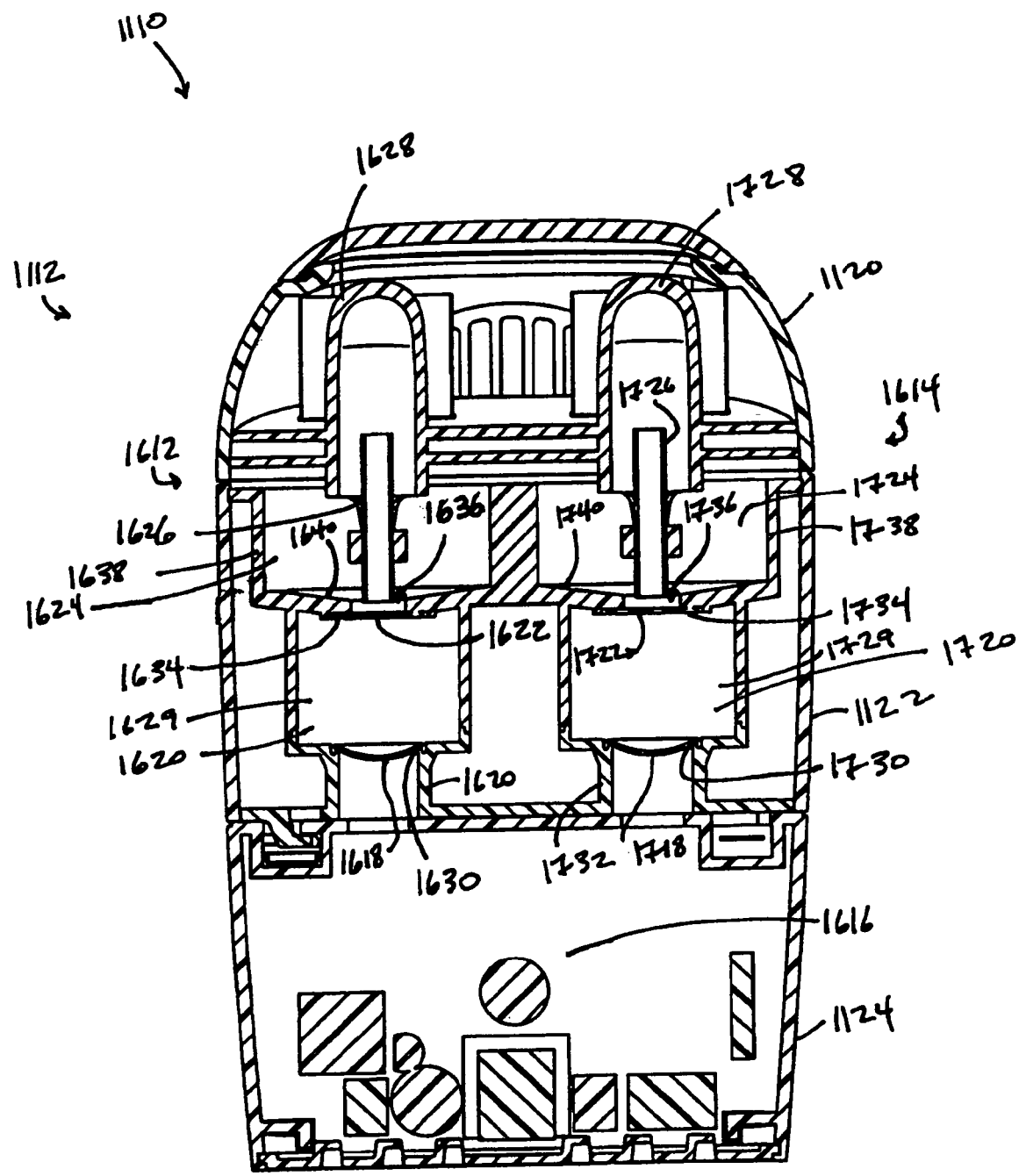

FIG. 13 is a cross sectional view of the nebulizing device of FIG. 11B, take along section line 13-13 FIG. 11B, according to one embodiment of the invention.

DETAILED DESCRIPTION OF THE PRESENTLY PREFERRED EMBODIMENTS OF THE INVENTION

FIG. 1 is a front perspective view, and FIG. 2A is a top view of a nebulizing device 110, according to an embodiment of the invention. Nebulizing device 110 is adapted to nebulize and deliver a drug solution to a user. Nebulizing device 110 provides various advantages in nebulizing and/or delivering the drug solution to the user. For example, nebulizing device 110 is capable of nebulizing viscous drug solutions such as drug solutions containing a surfactant, or other viscous drug solutions, delivers the drug solution at an enhanced flow rate, and provides other advantages as described herein. As shown, nebulizing device 110 includes a housing 112, a gas inlet 114, a nebulized drug delivery outlet 116, and a user control interface 118.

In one embodiment of the invention, housing 112 includes a plurality of housing members. Housing 112 includes an upper housing portion 120, a middle housing portion 121, and a lower housing portion 122. The front surface of upper housing portion 120 has a step region 124 formed thereon. Specifically, upper housing portion 120 has a top surface 126, an angled surface 128 extending downwardly from top surface 126, and a longitudinal horizontal ledge surface 130 extending outwardly from the bottom of angled surface 128. Thus, top surface 126 and ledge surface 130 are formed as offset parallel planar surfaces with angled surface 128 structurally joining top surface 126 and ledge surface 130 to form step region 124.

According to one embodiment of the invention, gas inlet 114 includes one or more inlet ports 132 formed in housing 112. Inlet ports 132 are located at middle housing portion 121 of housing 112.

The nebulized drug delivery outlet 116 includes a first outlet port 134 and a second outlet port 136. First outlet port 134 and second outlet port 136 are formed in housing 112 at angled surface 128. In an alternate embodiment, first outlet port 134 and second outlet port 136 may be formed as a single outlet port.

User control interface 118 includes a control knob 138. Control knob 138 is located on housing 112. In a non-limiting example, control knob 138 is located at lower housing portion 122 of housing 112. Of course, various other user interfaces could be used without departing from the scope of the present invention such as keypads, touch screens, wirelessly via a memory storage device, sent over a radio frequency, or Infrared communication link.

Figure 4:
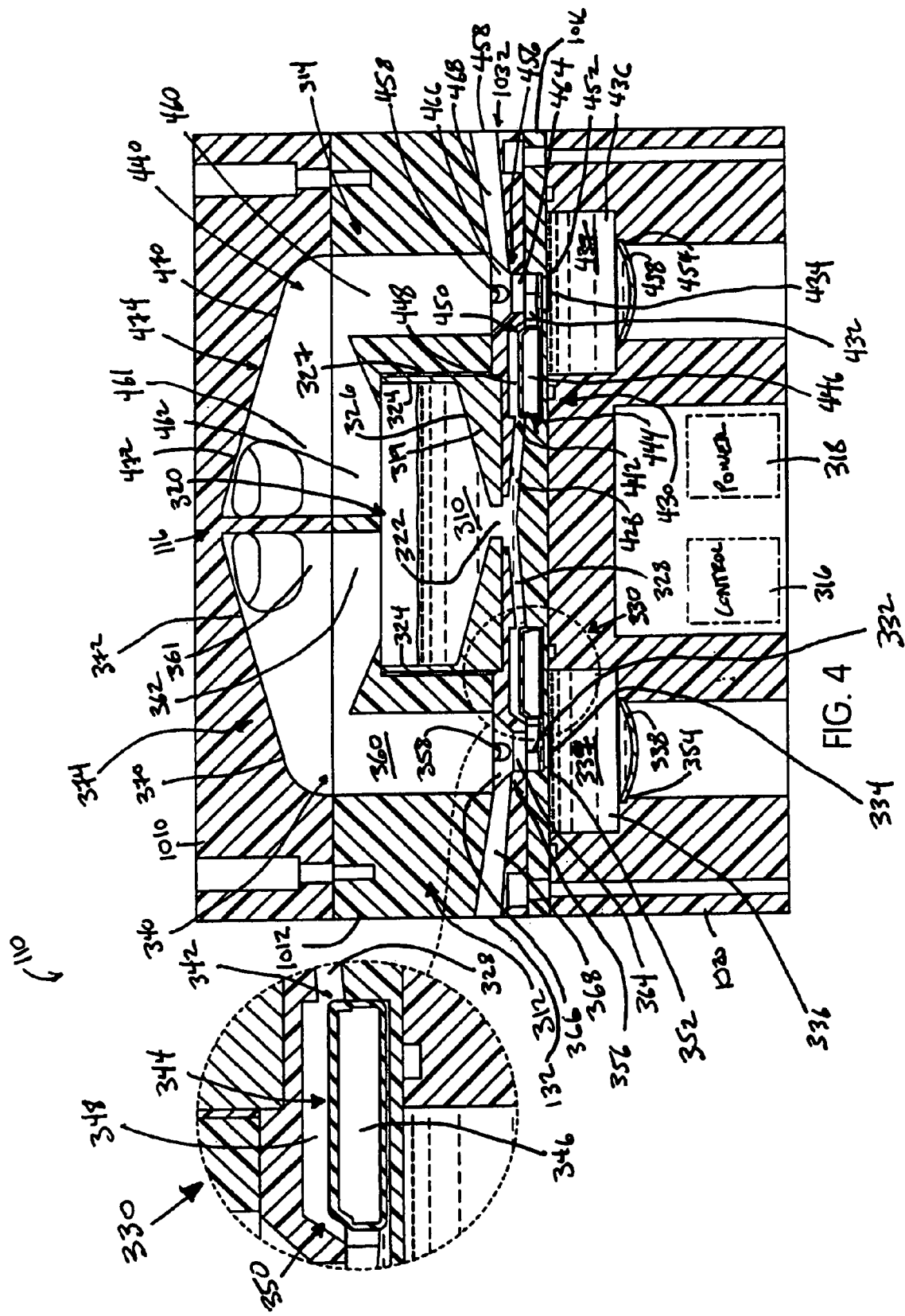

FIGS. 3 and 4 are cross sectional views, taken along cross section line 3-3, as illustrated in FIG. 2A, of nebulizing device 110. Referring to FIG. 3, nebulizing device 110 includes a drug solution reservoir 310, a first nebulization section 312, a second nebulization section 314, control electronics 316, and a power source/connection 318.

Drug solution reservoir 310 is contained in a reservoir housing member 319, included within housing 112. Drug solution reservoir 310 includes an upper drug solution receiving opening 320, a drug dispensing opening 322, a reservoir wall 324, and a reservoir floor 326. Drug solution reservoir wall 324 is generally cylindrical in shape, or may be otherwise shaped. Drug solution receiving opening 322 is defined by the upper periphery of reservoir wall 324, and is circular, or otherwise shaped. Reservoir floor 326 angles from reservoir wall 324 in a downward slope to drug dispensing opening 322 formed within reservoir floor 326.

Figure 5:
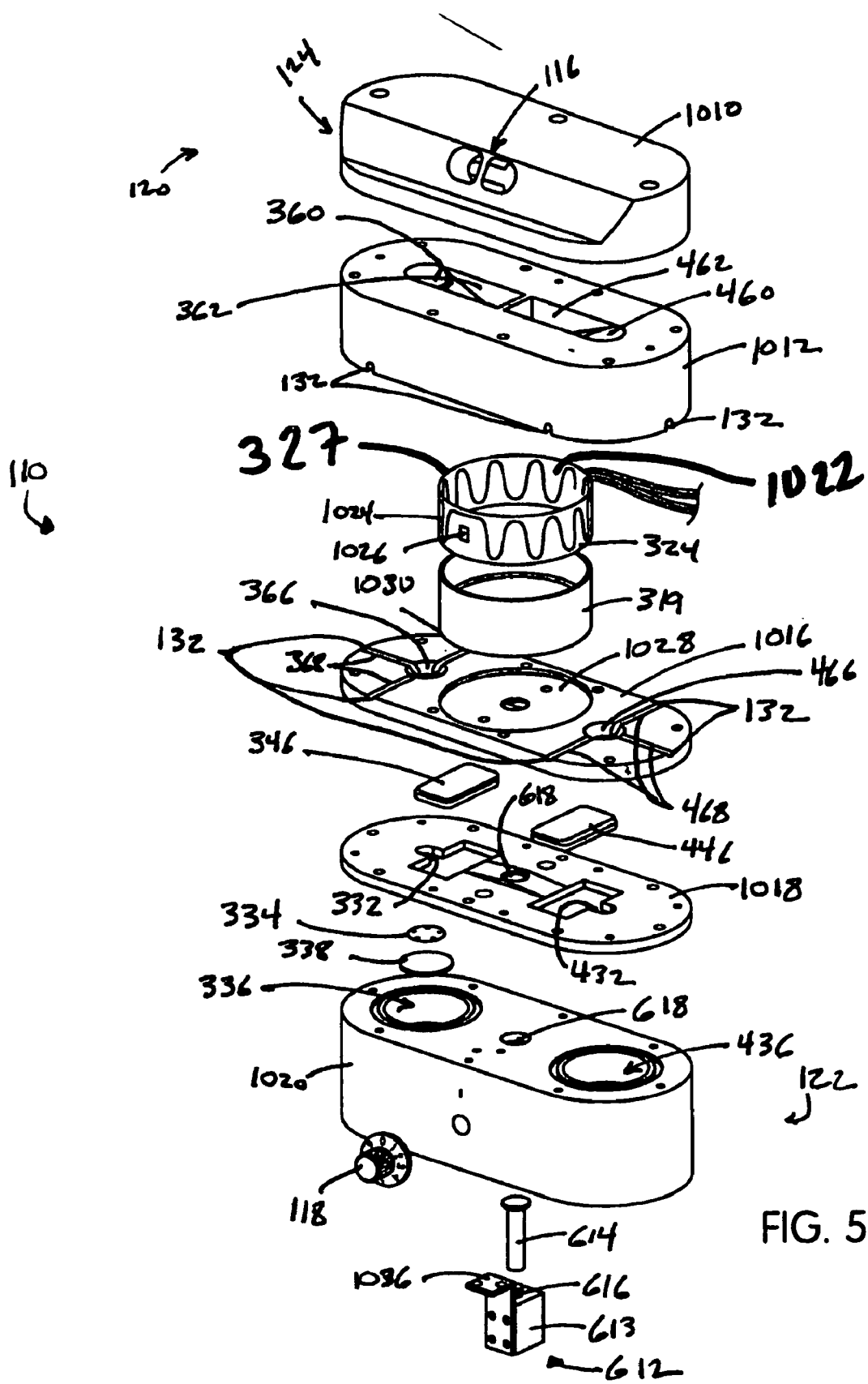

In one embodiment of the invention, the nebulizing device 110 also includes a heating/sensor unit 327 for heating the drug solution. This may be useful with higher viscosity drug solutions, or for increased comfort of a user. For example, to warm the drug solution prior to inhalation in instances when the device and/or drug solution contained therein have been exposed to cold temperatures. As shown in the embodiments of FIGS. 3-8 and as can be particularly appreciated from the exploded view of the embodiment of FIG. 5, heating/sensor unit 327 may be annularly disposed about the outer wall 324 that contains drug reservoir 310. As illustrated in FIG. 5, heating/sensor unit 327 may include an annular band member 1022, with a resistive heating element (or heater) 1024 and a temperature sensor 1026 disposed thereon. The temperature sensor 1026 within heating/sensor unit 327 is in functional communication with the heater 1024, to sense a temperature of the drug solution or the heater 1024 itself. Heating/sensor unit 327 is operatively coupled to one or both of control electronics 316 and power source/connection 318. Heating/sensor unit 327 is controlled via control electronics 316, and is powered via power source/connection 318.

The heater is operable in response to the temperature sensor 1026. In some instances, heating/sensor unit 327 maintains the temperature of the heater 1024 in a temperature range between an upper threshold temperature and a lower threshold temperature. Or, heating/sensor unit 327 maintains the temperature of the heater 1024 above a threshold temperature. It is contemplated that heating/sensor unit 327 is configured and/or arranged to heat the drug solution in at least one of drug reservoir 310, first barrier chamber 332, second barrier chamber 432, first reservoir channel 328, second reservoir channel 330, first aerosol region 340, and/or second aerosol region 440.

In another embodiment, the heater/sensing unit 327 can be separated so that either the heater or the sensor is disposed within the drug solution reservoir 310, in contact with the drug solution, and the other element (heater or sensor) is in contact with the outer wall 324 that contains drug reservoir 310. The sensor 1026 may be a thermocouple or other temperature sensing element such as a thermistor, resistance thermal detector, bimetallic, or Infrared.

It is further contemplated that the heater element 1024 need not be a resistive heater, but can be any suitable heater that can be used to raise the temperature of the drug solution.

According to various embodiments of the invention, first nebulization section 312 includes a first reservoir channel 328, a first valve 330, a first barrier chamber 332, a first barrier 334, a first fluid chamber 336, transmitting fluid 337, a first aerosol generator 338, and a first aerosol region 340. First reservoir channel 328 is formed within housing 112 and runs from drug dispensing opening 322 to first valve 330. First valve 330 is positioned outwardly from drug dispensing opening 322 within housing 112, between first reservoir channel 328 and first barrier chamber 332.

In one embodiment, seen best in FIG. 4, first valve 330 includes a first valve opening 342, and a valve seal 344. First valve opening 342 is formed within housing 112 as an outer opening of first reservoir channel 328. First valve structure 344 is disposed at first valve opening 342 to selectively seal first valve opening 342. In one embodiment, first valve structure 344 includes a first float 346, disposed within first valve 330 at a first float reception cavity 348. First float 346 is composed of a material that enables first float 346 to float in the drug solution, such as, for example, a closed cell foam. First float reception cavity 348 is formed in housing 112 between first reservoir channel 328 and first barrier chamber 332. First valve 344 includes a first float/cavity interface 350 that includes corresponding surfaces of first float 346 and first float reception cavity 348. First float 346 seals first valve opening 342 as first float 346 rises to seal first valve opening 342. For example, as is illustrated in FIGS. 3, and 4, first float/cavity interface 350 includes corresponding angled surfaces of first float 346 and first float reception cavity 348.

Figure 6:
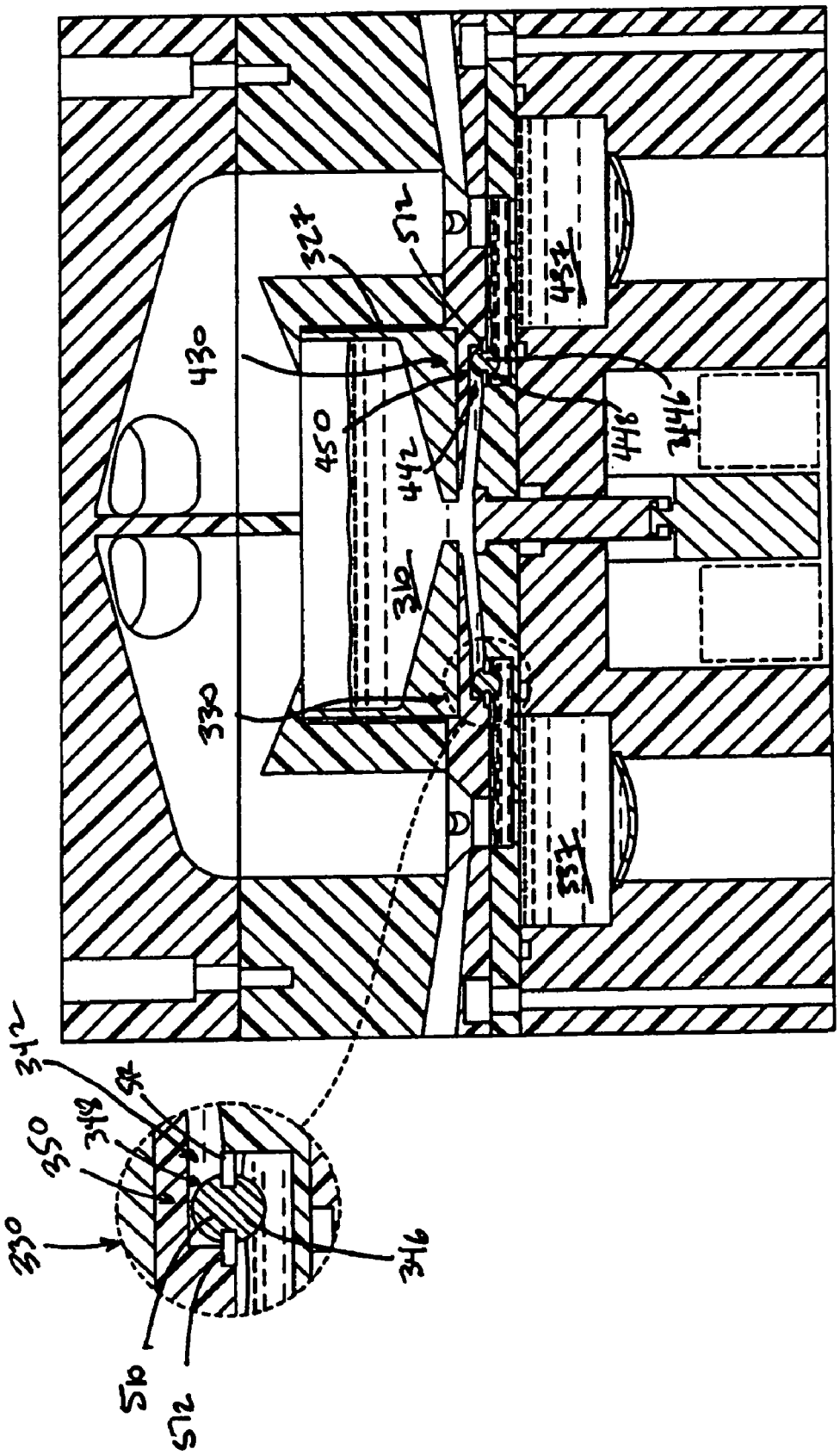

Referring to FIG. 6, an exemplary illustration of nebulizing device 110 provides an alternate configuration for valves 330 and 430. According to the embodiment illustrated in FIG. 6, floats 346 and 446 include a body 510 and an annular protrusion 512. Annular protrusion 512 surrounds body 510, and extends outward from body 510 in a direction normal to the surface of body 510 that annular protrusion 512 protrudes from. As floats 346 and 446 rise up to contact float/cavity interfaces 350 and 450, bodies 510 of floats 346 and 446 contact an upper surfaces 514 of float cavities 348 and 448, annular protrusions 512 effectively seal valve openings 342 and 442, closing valves 330 and 430.

In other embodiments, valves 330 and 430 may take the form of one or more electrically operated solenoid valves. Such valves can each be open in response to an associated liquid level detector that detects the amount of drug solution on one of the barriers. When the detector detects that the amount of drug solution is at or below a threshold level, it sends a signal that is used to open the associated valve and permit the drug solution to flow from the associated reservoir to the associated barrier. In such an embodiment, the liquid level detector can optionally be an adjustable detector to enable the threshold level at which the drug solution will be released from the reservoir to the barrier to be adjusted.

In the embodiment illustrated in FIGS. 3, and 4, first barrier chamber 332, which communicates with first reservoir channel 328 via first valve 330 is formed within housing 112 between first barrier 334 and first aerosol region 340. First barrier 334 is mounted within housing 112 to a first mounting surface 352 that is formed on an upper surface of first fluid chamber 336, between first barrier chamber 332 and first fluid chamber 336. First barrier forms a physical separation (i.e., a seal) between first barrier chamber 332 and first fluid chamber 336. First barrier 334 is composed of one or more materials designed to enable first barrier 334 to be capable of transmitting ultrasonic energy therethrough, even under high temperature conditions. For example, polyetheretherketone (PEEK), or other materials may be used.

According to one embodiment of the invention, first fluid chamber 336 is formed within housing 112 between first barrier 334 and first aerosol generator 338. In one embodiment, the first aerosol generator 338 is an acoustic wave generator, such as a piezoelectric transducer, and first fluid chamber 336 holds a fluid 337 in communication with first barrier 334 and first aerosol generator 338. Fluid 337 can be selected to be capable of transmitting acoustic waves, such as, for example, water, or other fluids. Fluid 337 may include one or more sterilants, such as, alcohol, or other sterilants.

In one embodiment of the invention, first aerosol generator 338 is disposed at a first seating portion 354 formed within housing 112. In embodiments where first aerosol generator 338 comprises a piezoelectric transducer, it may be formed to have a concave configuration with a silver electrode. First aerosol generator 338 generates acoustic waves at a generator frequency, such as, for example, 2.5 MHz, or another frequency. The acoustic waves are focused at a focal point, or focal band, that is a focal length from first aerosol generator 338. First seating portion 354 is formed within housing 112 such that the focal point will be within first barrier chamber 332. First aerosol generator 338 is operatively linked to control electronics 316 so that control electronics 316 can control various aspects of acoustic wave generation by first aerosol generator 338, such as, for instance, activation and deactivation. First aerosol generator 338 is operatively linked to power source/connection 318 so that power can be provided to first aerosol generator 338 via this operative link.

Power source/connection 318 may include a power cord 140. Power cord 140 can be connected to a contemporary household socket to deliver power to the nebulizing device 110. Cord 140 could have a fixed length or could have a mechanism to retract a majority of cord 140 into housing 112. This feature of the present invention could be used regardless of the aerosol generator being used. The present invention contemplates that cord 140 could also be used with a variety of nebulizers including jet nebulizers, traditional planar ultrasonic nebulizers, vibrating mesh nebulizers, vibrating plate nebulizers, or electro spray nebulizers. The unique advantage this feature of the present invention provides is that it prevents cord 140 from becoming tangled with objects present in the user's environment when not in use.

According to an embodiment of the invention, first aerosol region 340 includes a first fountain region 356, one or more first aerosol region inlets 358, a first chimney 360, a first drug delivery region 361, and a first drug return region 362. First fountain region 356 is formed within housing 112 between first barrier chamber 332 and first chimney 360. First fountain region 356 includes a lower first fountain region 364 and an upper first fountain region 366. Lower first fountain region 364 is open at a first end to first barrier chamber 332 and at a second end to upper first fountain region 366. Lower first fountain region 364 is cylindrical, or may be otherwise shaped. Upper first fountain region 366 is open at a first end to lower first fountain region 364 and at a second end to first chimney 360. Upper first fountain region 364 is formed as a funnel with a smaller opening at the first end and a larger opening at the second end, or may be otherwise shaped.

As is illustrated in FIGS. 3, and 4, first aerosol region inlets 358 are formed in housing 112 at first fountain region 356. First aerosol region inlets 358 provide an opening for one or more corresponding inlet channels 368. Inlet channels 368 are formed in housing 112, and run between first aerosol region inlets 358 and inlet ports 132.

In one embodiment, first chimney 360 is formed in housing 112, and opens at a first end to first fountain region 356. A first chimney ceiling 370 is formed within housing 112 at a second end of first chimney 360. At a side of first chimney 360, proximate to first chimney ceiling 370, first chimney 360 opens to first drug delivery region 361.

According to an embodiment of the invention, first drug delivery region 361 is formed within housing 112 to communicate with first chimney 360, first outlet port 134, and first drug return region 361. First drug delivery region 361 is open to first drug return region 361 at a first end, and is bounded at a second end by first drug delivery region ceiling 372. First drug delivery region ceiling 372 and first chimney ceiling 370 form a first aerosol region ceiling 374.

In one embodiment of the invention, first drug return region 362 is formed in housing 112 to be open at a first end to drug reservoir 310. First drug return region 362 also communicates with first drug delivery region 361.

According to the embodiment of the invention shown in FIGS. 3, 4, second nebulization section 312 includes a second reservoir channel 428, a second valve 430, a second barrier chamber 432, a second barrier 434, a second fluid chamber 436, a second fluid 437 within second fluid chamber 436, a second aerosol generator 438, and a second aerosol region 440. Second reservoir channel 428 is formed within housing 112 and runs from drug dispensing opening 422 to second valve 430. Second valve 430 is positioned outwardly from drug dispensing opening 422 within housing 112, between second reservoir channel 428 and second barrier chamber 432.

The invention contemplates that first aerosol generator 338 and second aerosol generator 438 may be any device capable of forming aerosol. For instance, the unique aspects of the present invention can also be used with compressor driven jet nebulizers, traditional planar ultrasonic nebulizers, vibratory mesh nebulizers, vibrating plate nebulizers, or electrospray nebulizers without departing from the teachings of the present invention.

The second valve 430 includes a second valve opening 442, and a valve seal 444. Second valve opening 442 is formed within housing 112 as an outer opening of second reservoir channel 428. Second valve seal 444 is disposed at second valve opening 442 to selectively seal second valve opening 442. In some instances, second valve seal 444 includes a second float 446, disposed within second valve 430 at a second float reception cavity 448. Second float 446 is composed of materials that enable second float 446 to float in the drug solution. Second float reception cavity 448 is formed in housing 112 between second reservoir channel 428 and second barrier chamber 432. Second valve 444 includes a second float/cavity interface 450 that includes corresponding surfaces of second float 446 and second float reception cavity 448, and is arranged to bias second float 446 against second valve opening 442 as second float 446 rises to seal second valve opening 442. For example, as is illustrated in FIGS. 3, and 4, second float/cavity interface 450 includes corresponding angled surfaces of second float 146 and second float reception cavity 448.

According to an embodiment of the invention, second barrier chamber 432, which communicates with second reservoir channel 428 via second valve 430 is formed within housing 112 between second barrier 434 and second aerosol region 440. Second barrier 434 is mounted within housing 112 to a second mounting surface 452 that is formed on an upper surface of second fluid chamber 436, between second barrier chamber 432 and second fluid chamber 436. Second barrier forms a physical separation (i.e., a seal) between second barrier chamber 432 and second fluid chamber 436. Second barrier 434 is composed of one or more materials designed to enable second barrier 434 to be capable of transmitting ultrasonic energy therethrough, even under high temperature conditions. For example, polyetheretherketone (PEEK), or other materials may be used.

In accordance with the embodiment of the invention illustrated in FIGS. 3, and 4, second fluid chamber 436 is formed within housing 112 between second barrier 434 and second aerosol generator 438. The aerosol generator 438, in one embodiment, is a concave shaped piezoelectric transducer with a silver electrode. The piezoelectric aerosol generator 438 achieves its functionality by generating acoustic waves in the drug solution as described with respect to the first aerosol generator 338. Second fluid chamber 436 holds a fluid in communication with second barrier 434 and second aerosol generator 438. Fluid 337 includes one or more fluids capable of transmitting acoustic waves, such as, for example, water, or other fluids. Fluid 337 may include one or more sterilants, such as, alcohol, or other sterilants.

In one embodiment of the invention, second aerosol generator 438 is disposed at a second seating portion 454 formed within housing 112. In some instances, second aerosol generator 438 includes a concave piezoelectric transducer with a silver electrode. Second aerosol generator 438 generates acoustic waves at a generator frequency, such as, for example, 2.5 MHz, or another frequency. The acoustic waves are focused at a focal point, or focal band, that is a focal length from second aerosol generator 438. Second seating portion 454 is formed within housing 112 such that the focal point will be within second barrier chamber 432. Other embodiments of second aerosol generator 438 exist. Second aerosol generator 438 is operatively linked to control electronics 316 so that control electronics 316 can control various aspects of acoustic wave generation by second aerosol generator 438, such as, for instance, activation and deactivation, or other aspects. Second aerosol generator 438 is operatively linked to power source/connection 318 so that power can be provided to second aerosol generator 438 via this operative link.

The second aerosol region 440 includes a second fountain region 456, one or more second aerosol region inlets 458, a second chimney 460, a second drug delivery region 461, and a second drug return region 462. Second fountain region 456 is formed within housing 112 between second barrier chamber 432 and second chimney 460. Second fountain region 456 includes a lower second fountain region 464 and an upper second fountain region 466. Lower second fountain region 464 is open at a first end to second barrier chamber 432 and at a second end to upper second fountain region 466. Lower second fountain region 464 is cylindrical, or may be otherwise shaped. Upper second fountain region 466 is open at a first end to lower second fountain region 464 and at a second end to second chimney 460. Upper second fountain region 464 is formed as a funnel with a smaller opening at the first end and a larger opening at the second end, or may be otherwise shaped.

In one embodiment of the invention, second aerosol region inlets 458 are formed in housing 112 at second fountain region 456. Second aerosol region inlets 458 provide an opening for one or more corresponding inlet channels 468. Inlet channels 468 are formed in housing 112, and run between second aerosol region inlets 458 and inlet ports 132.

In one embodiment, second chimney 460 is formed in housing 112, and opens at a first end to second fountain region 456. A second chimney ceiling 470 is formed within housing 112 at a first end of second chimney 460. At a side of second chimney 460, proximate to second chimney ceiling 470, second chimney 460 opens to second drug delivery region 461.

According to the embodiment of the invention shown in FIGS. 3, and 4, second drug delivery region 461 is formed within housing 112 to communicate with second chimney 460, second outlet port 134, and second drug return region 461. Second drug delivery region 461 is open to second drug return region 461 at a first end, and is bounded at a second end by second drug delivery region ceiling 472. Second drug delivery region ceiling 472 and second chimney ceiling 470 form a second aerosol region ceiling 474.

The second drug return region 462 is formed in housing 112 to be open at a first end to drug reservoir 310. Second drug return region 462 also communicates with second drug delivery region 461.

According to an embodiment of the invention, barrier chambers 332 and 432 hold an amount of the drug solution at each of barriers 334 and 434. Fountains are formed at barrier chambers 332 and 432. The fountains create nebulized particles of the drug solution that are delivered to aerosol regions 340 and 440. The nebulized particles of the drug solution are formed by acoustic waves within the drug solution held in barrier chambers 332 and 432 at barriers 334 and 434. The acoustic waves are generated by aerosol generators 338 and 438. The acoustic waves transmitted from aerosol generators 338 and 438 to barrier chambers 332 and 432 via the fluid held in fluid chambers 336 and 436. The transmitted acoustic waves pass from fluid chambers 336 and 436 to barrier chambers 332 and 432 via barriers 334 and 434.

In accordance with the embodiment of the invention illustrated in FIGS. 3, and 4, the acoustic waves transmitted to barrier chambers 332 and 432 are focused at the focal point. The drug solution in barrier chambers 332 and 432 absorbs the ultrasonic energy provided by the focused acoustic waves to create a fountain within each of barrier chambers 332 and 432. The ultrasonic energy delivered by the acoustic waves has a maximum density at or near the focal point of the acoustic waves. The fountains shed a portion of the drug solution as particles. Some of these particles are so large they immediately fall out. Some are small enough to pass into drug return regions 362,462 before falling out. The remaining particles which are appropriately sized, pass out through first and second outer ports 134,136. In this manner, substantially consistent particle size is achieved.

In one embodiment of the invention, the nebulized particles are communicated from barrier chambers 332 and 432, through aerosol regions 340 and 440, and to the user via outlet ports 134 and 136 included in outlet 116. More particularly, the nebulized particles and the larger droplets of the drug solution formed at the fountains are received by aerosol regions 340 and 440 at fluid chambers 364 and 464, and pass into chimneys 360 and 460. From chimneys 360 and 460, the nebulized particles are communicated to the user via drug delivery regions 361 and 461 and outlet ports 134 and 136. In contrast, due to size and/or weight, the larger droplets may not be communicated to the user, but instead may contact a surface of aerosol regions 340 and 440, such as aerosol ceilings 372 and 472, or other surfaces. The larger droplets then condense on the contacted surface(s), thereby separating the larger droplets from the nebulized particles prior to delivery to the user. The condensed larger droplets are passed back to drug solution reservoir 310 via drug return regions 362 and 462.

The nebulization of the drug solution at the fountains is enhanced when the focal point of the acoustic waves coincides (exactly or substantially) with an upper surface of the drug solution in first barrier chamber 332. This requires a level of the upper surface to be controlled with some particularity to enhance the operation of the fountains. To control the level of the upper surface, a flow of the drug solution from drug reservoir 310 to barrier chambers 332 and 432 via reservoir channels 328 and 428 are controlled via valves 330 and 430 by independently sealing and unsealing valve openings 342 and 442 with valve seals 344 and 444. For example, when the level of the upper surface of the drug solution on either of barriers 334 and/or 434 reaches a threshold level at or near the focal point of the acoustic waves, corresponding ones of floats 346 and/or 446 are positioned to seal valve openings 342 and/or 442 by virtue of the buoyancy of floats 346 and 446 with respect to the drug solution. However, as particles are formed at the fountains, the level of the upper surface in one or both of barrier chambers 332 and 432 may drop below the threshold level, which in turn lowers one or both of floats 346 and 446 from valve openings 342 and 442, thereby opening valves 330 and/or 430, as is illustrated in FIG. 4.

Referring to FIG. 3, in some embodiments of the invention, activation of aerosol generators 338 and 438 enable generation of particles of the drug solution to be propelled by the fountains into aerosol regions 340 and 440. As particles are propelled by the fountain into aerosol regions 340 and 440, the atmosphere within aerosol regions 340 and 440 is disturbed such that intake gas present within inlet channels 368 and 468 is pulled into particle receiving regions 366 and 466 via aerosol region inlets 358 and 458. Pulling air into particle receiving regions 366 and 466 may initiate the flow of intake gas through aerosol regions 340 and 440 to outlet ports 134 and 136, which may in turn motivate the nebulized particles formed at the fountains toward outlet ports 134 and 136. Thus, the atmospheric disturbances that may be caused by the nebulized particles from the fountains, and the resulting flow of intake gas through aerosol regions 340 and 440 may function in a cooperative manner to "drive" the delivery of nebulized particles from the fountains to the user without requiring additional active moving parts such as a pump or compressor.

FIG. 5 is an exploded view of nebulizing device 110 according to an embodiment of the invention. Housing 112 includes an outlet housing member 1010, a drug return housing member 1012, a reservoir housing member 319, a drug reservoir seating member 1016, a barrier chamber housing member 1018, and a base housing member 1020.

The outlet housing member 1010 is disposed at the upper housing portion 120 of housing 112. Outlet 116 is formed in outlet housing member 1010. As may be seen in FIGS. 3, 4, 7, and 8 illustrating cross sections taken along cross section line 3, show various components of aerosol regions 340 and 440 are formed within outlet housing member 1010. For example, aerosol region ceilings 374 and 474, and drug delivery regions 361 and 461 are formed within outlet housing member 1010.

According to one embodiment of the invention, drug return housing member 1012 may be disposed adjacent outlet housing member 1010. As may be seen in the FIGS. 3, 4, 7, and 8 illustrating cross sections taken along cross section line 3-3, show various components of aerosol regions 340 and 440 are formed within drug return housing member 1012. For example, chimneys 360 and 460, and drug return regions 362 and 462 are formed within drug return housing member 1012. Inlet ports 132 of gas inlet 114, and corresponding inlet channels 368, are partially formed in drug return housing member 1012.

In the embodiment illustrated in FIG. 5, heating/sensor unit 327 is disposed around an outer surface of reservoir housing member 319. Drug return housing member 1012 may be adapted to receive heating/sensor unit 327 and reservoir housing member 319. Reservoir housing member 319 is disposed primarily within drug return housing member 1012, and forms drug reservoir 310.

According to various embodiments of the invention, drug reservoir seating member 1016 is disposed adjacent to drug return housing member 1012. A drug reservoir seating portion 1028 is formed on drug reservoir seating member 1016. Drug reservoir seating portion 1028 is configured to receive a seating portion 1030 of reservoir housing member 319 therein. Upper fluid chambers 366 and 466 are formed in drug reservoir seating member 1016. Inlet ports 132 of gas inlet 114, and corresponding inlet channels 368, are partially formed in drug reservoir seating member 1016. As may be seen in FIGS. 3, 4, 7, and 8 illustrating cross sections taken along cross section line 3-3, when drug reservoir seating member 1016 is disposed adjacent to drug return housing member 1012, inlet ports 132 of gas inlet 114, and the corresponding inlet channels 368 are formed in housing 112 at an inlet interface 1032 between drug return housing member 1012 and drug reservoir seating member 1016.

As is illustrated in FIG. 5, barrier chamber housing member 1018 is disposed in housing 112 adjacent to drug reservoir seating member 1016. Barrier chambers 332 and 432, and an upper portion of a plunger channel 618 are formed in barrier chamber housing member 1018. When barrier chamber housing member 1018 is disposed in housing 112 adjacent to drug reservoir seating member 1016 a valve interface 1034 is formed. As may be seen in FIGS. 3, 4, 7, and 8 illustrating cross sections taken along cross section line 3, reservoir channels 328 and 428, and valves 342 and 442 are formed at valve interface 1034. Also illustrated in FIGS. 3, 4, 7, and 8, barrier chamber housing member 1018 includes mounting surfaces 352 and 452.

Returning to FIG. 5, base housing member 1020 is disposed adjacent to barrier chamber housing member 1018, at lower housing portion 122 of housing 112, forming a base for housing 112. Base housing member 1020 may form fluid chambers 336 and 436, solenoid cavity 610, and a lower portion of plunger channel 618. A solenoid 612 is mounted within solenoid cavity 610 via solenoid bracket 1036. Aerosol generator 338 is seated within base mounting member 1020 at seating portion 354, formed therein. Base mounting member 1020 is adapted to receive user control interface 118.

It will be appreciated that the configurations of housing 112 shown, including housing members 1010, 1012, 319, 1016, 1018, and 1020 are illustrated for exemplary purposes only, and that other embodiments of housing 112 and its various members exist.

Figure 7:
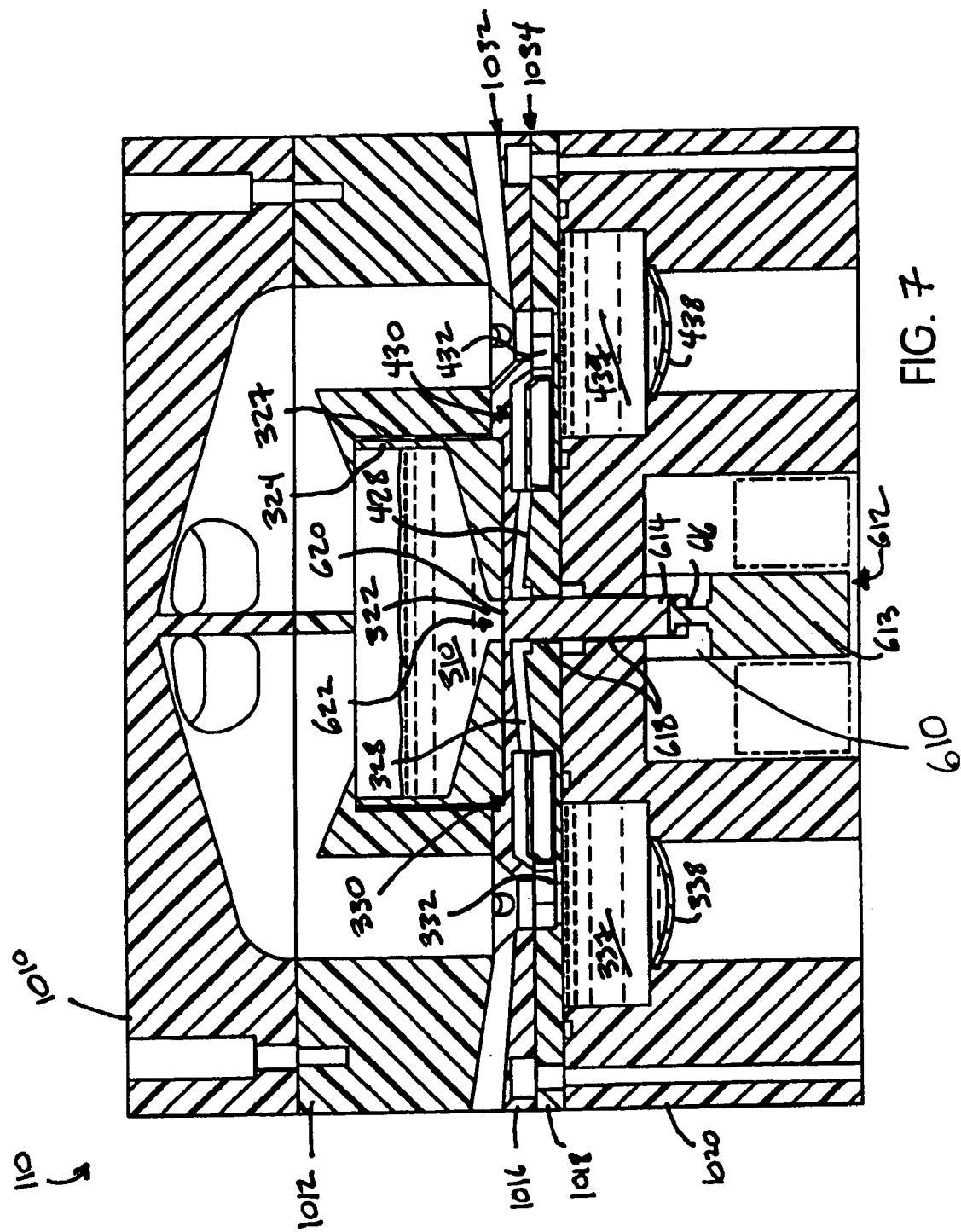
Figure 8:
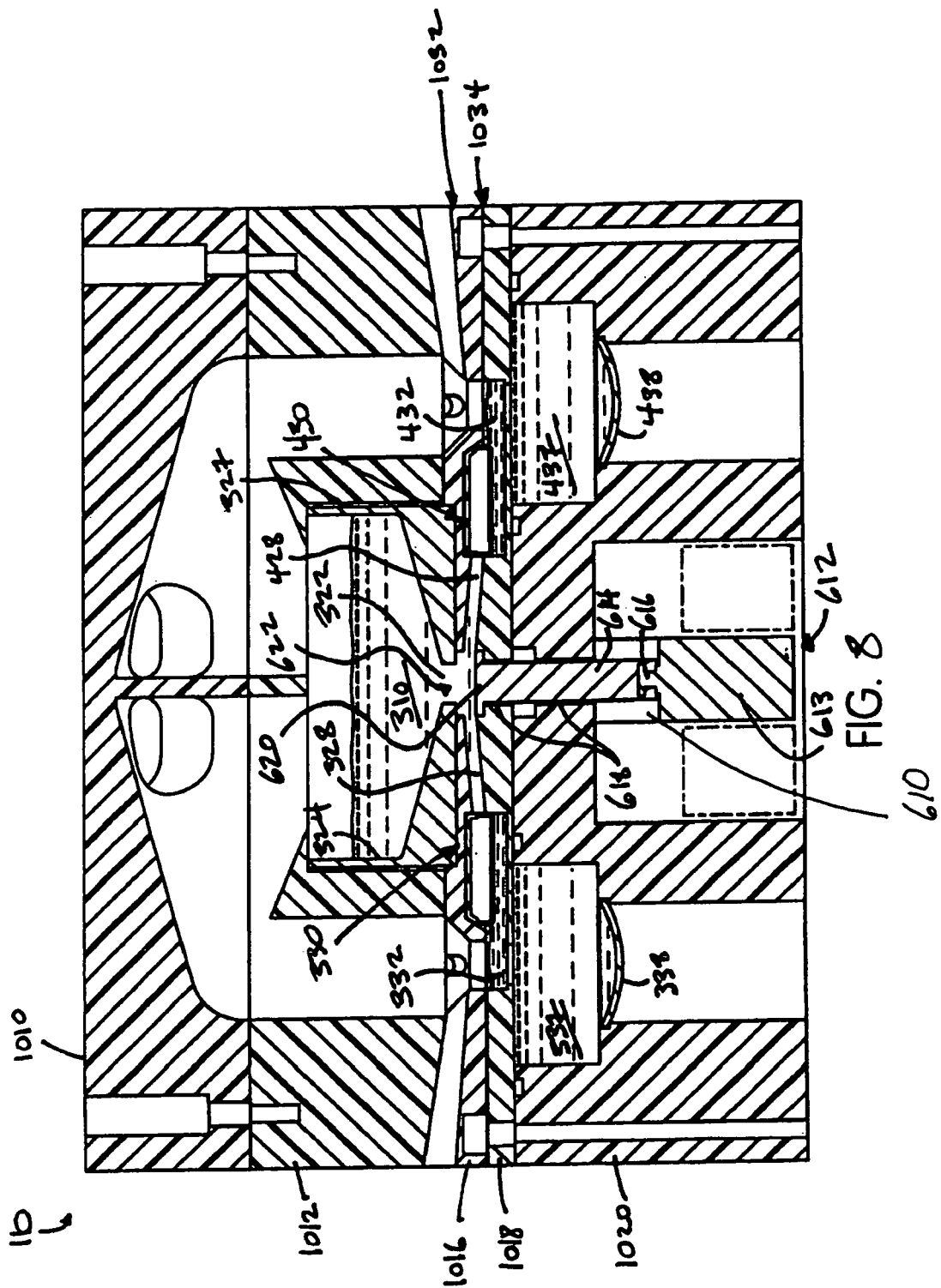

FIGS. 7 and 8 illustrate another embodiment of the invention that enables the drug solution held within housing 112 to be heated prior to, during, and/or after nebulization. The drug solution may be heated to enhance a comfort of the user, to lower a viscosity of the drug solution to augment nebulization of the drug solution, increase drug delivery flow rate, or for other purposes.

As illustrated in FIGS. 7 and 8, nebulizing device 110 includes a solenoid cavity 610 formed in housing 112. A solenoid 612 is mounted in solenoid cavity 610. Solenoid 612 has a solenoid body 613 and a solenoid shaft 616, which is joined to a movable plunger 614. In FIG. 7, the solenoid is shown energized, while in FIG. 8 it is de-energized. When the solenoid 612 is actuated, shaft 616 extends from the solenoid body 613. Of course one of ordinary skill in the art can best appreciate that the solenoid could be reconfigured so that when it is energized it retracts into the solenoid body.

Plunger 614 is joined to the solenoid body 613 at a first end and includes a plunger head 620 at a second end. Plunger head 620 interacts with drug dispensing opening 322 to comprise a reservoir valve 622. Plunger 614 is actuated between the engaged position (illustrated in FIG. 7) and the disengaged position (illustrated in FIG. 8) to open and close reservoir valve 622. In the engaged position, plunger head 620 engages drug dispensing opening 322 of drug solution reservoir 310 such that plunger head 620 seals drug dispensing opening 322. Sealing drug dispensing opening 322 keeps the drug solution in drug solution reservoir 310 from flowing to barrier chambers 332 and 432 along reservoir chambers 328 and 428 respectively. In the disengaged position, plunger head 620 is withdrawn from drug dispensing opening 322 to enable the drug solution held in drug solution reservoir 310 to flow to barrier chambers 332 and 432. Solenoid 612 is operatively coupled to control electronics 316 and power source/connection 318. Solenoid 612 is controlled via control electronics 316. Solenoid 612 is powered via power source/connection 318. It can be appreciated that while at rest, the solenoid 612 is positioned to seal the opening 322 and activated to unseal it, the opposite arrangement can alternatively be provided so that the solenoid 612 is activated to seal the opening and deactivated to unseal the opening 322

Figure 9:
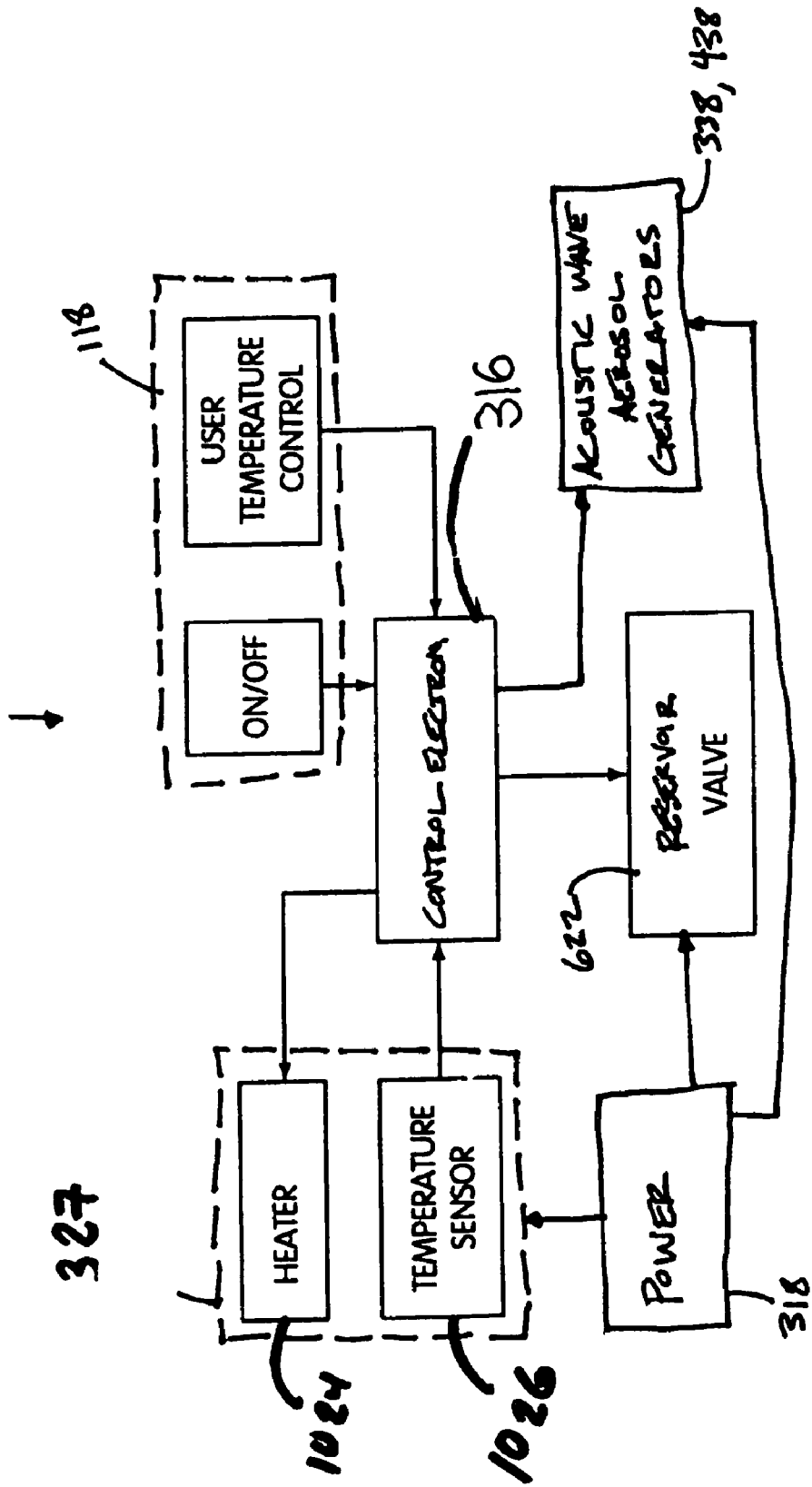

FIG. 9 is an exemplary illustration of circuitry 626 that may be used in nebulizing device 110 according to an embodiment of the invention. As shown, control electronics 316 are operatively linked with various components of nebulizing device 110, such as, for example, user control interface 118, power source/connection 318, aerosol generators 338 and 438, reservoir valve 622, heating/sensor unit 327, and/or other components.

FIG. 10 is an exemplary illustration of a method 910 of controlling a nebulizing device according to one embodiment of the invention. Method 910 is commenced from a state in which the device is deactivated. In this state, a drug solution is held in drug reservoir 310 with closed valve 622, the heater/sensing unit 327 associated with the device is at room temperature, and aerosol generators 338 and 438 associated with the device are deactivated.

An activation command is conveyed from the user to the device at an operation 912. For example, the activation commend is input via user control interface 138, or otherwise conveyed from the user to the device.

Method 910 includes an operation 914, at which a first threshold temperature and a second threshold temperature is determined. The first threshold temperature and/or the second threshold temperature is determined, in non-limiting examples, according to an input from the user, determined based on a default setting, determined automatically based on one or more measured variables, and/or otherwise determined. The inventors presently contemplate that the preferred operating temperature is 37 degrees Celsius or between 33 degrees to 41 degrees Celsius. Of course, delivery temperatures outside this range could also be used without departing from the scope of the present invention as dictated by the requirements of the particular drug being delivered and/or user preferences.

Method 910 includes an operation 916, at which the heater in heater/sensing unit 327 associated with the nebulizing device 110 is activated. Activating the heater includes transmitting power to the heater. Activation causes the temperature of the heater to rise.

As is shown in FIG. 10, method 910 includes an operation 918, at which the temperature of the heater associated with heater/sensing unit 327 is sensed to determine if the temperature is above the first temperature threshold. If the temperature of the heater is below the first threshold temperature, method 910 returns to operation 916.

If the temperature of the heater is above the first threshold temperature, method 910 proceeds to an operation 920. At operation 920, the drug solution is released from the drug reservoir 310 for nebulization. For example, the drug solution is released to barriers 334 and 434 by opening valve 622.

Method 910 includes an operation 922, at which aerosol generators 338 and 438 are activated. The acoustic waves generated by the activated aerosol generators 338 and 438 are delivered to the drug solution to form nebulized particles from the drug solution at corresponding ones of barriers 334 and 434.

Method 910 includes an operation 924, at which the temperature of the heater is sensed by the temperature sensor to determine if the temperature is between the first temperature and the second temperature. If the temperature of the heater is determined to be below the first temperature, method 910 proceeds to an operation 926. At operation 926, the flow of the drug solution from the drug reservoir 310 to the barriers 334 and 434 are sealed (or substantially sealed), effectively stopping the delivery of the drug solution from the drug reservoir 310 to the barriers 334 and 434. For example, the flow of the drug solution is sealed by closing valve 622. At operation 926, the aerosol generators 338 and 438 are deactivated. From operation 926, method 910 may return to operation 916.

As is illustrated in FIG. 10, at operation 924, if the temperature of the heater is above the first threshold and the second threshold, method 910 proceeds to an operation 928, at which the heater is deactivated. This causes the heater to stop producing heat. In some instances, the flow of the drug solution from the drug reservoir 310 to the barriers 338 and 438 is sealed (or substantially sealed), effectively stopping the delivery of the drug solution from the drug reservoir 310 to the barriers 334 and 434, and the aerosol generators 338 and 438 are deactivated. However, in other instances, the delivery of the drug solution from the drug reservoir 310 to the barriers 334 and 434 is continued and the aerosol generators 338 and 438 are deactivated. From operation 928, method 910 returns to operation 924.

At operation 924, if the temperature of the heater is between the first temperature threshold and the second temperature threshold, method 910 proceeds to an operation 930. At operation 930, it is determined if a treatment session with the nebulizing device 110 has been completed. The completion of a treatment session includes, among other things, receiving a deactivation command from the user, completing nebulization of a predetermined or threshold amount of the drug solution, nebulizing the drug solution for a predetermined or threshold amount of time, or otherwise completing the treatment session. If the treatment session is not completed, method 910 returns to operation 924. If the treatment session is completed, method 910 proceeds to an operation 932.

At operation 932, the nebulizing device 110 is deactivated. Deactivating the nebulizing device 110 includes, among other things, deactivating the aerosol generators 338 and 438, closing the valve 622, and/or otherwise deactivating the nebulizing device 110.

FIGS. 11A-11C and 12 are exemplary illustrations of a handheld nebulizing device 1110 in accordance with another embodiment. In this embodiment, device 1110 includes a housing 1112, an inlet 1114, an outlet 1116, and a user control interface 1118.

Housing 1112 includes mouthpiece module 1120, an intermediate module 1122, and a base module 1124. Modules 1120, 1122, and 1124 are selectively coupled to each other, and may be coupled and uncoupled to each other by the user.

As is illustrated in the rear plan view of FIG. 11C, inlet 1114 includes an inlet port 1121 formed in housing 1112, and particularly in mouthpiece module 1120.

As shown in the front plan view of FIG. 11A, outlet 1116 includes an outlet port 1126 formed in housing 1112 at mouthpiece module 1120. Outlet port 1126 is configured for engagement by the user's mouth.

In some embodiments, user control interface 1118 includes a control knob 1128. Control knob 1128 is located on the front of housing 1112 at base module 1124.

Intake gas, such as air from the atmosphere, is received into inlet 1114. At outlet 1116, nebulized particles of the drug solution are communicated from device 1110 to the user. The user may control various aspects of operation of device 1110 via control interface 1118.

As is illustrated in FIG. 11C, device 1110 includes a power receiving connector 1130. Power connector 1130 is provided in housing 1112 at base module 1124. Power is provided to device 1110 via power connection 1130. Alternatively, power may be provided to device 1110 via an internal power source, such as a battery, a fuel cell, or other power source.

FIG. 12 is a cross sectional view, taken along cross section line 12-12 in FIG. 11B. In some instances, device 1110 includes a drug solution reservoir 1310, a first nebulization section 1312, a second nebulization section 1314, and control electronics 1316.

Drug solution reservoir 1310 includes a drug solution receiving opening 1320, a drug dispensing opening 1322, a reservoir wall 1324, and a reservoir floor 1326. Drug solution reservoir 1310 is generally cylindrical in shape, or may be otherwise shaped. Drug solution receiving opening 1322 is formed by reservoir wall 1324, and is circular, or otherwise shaped. Reservoir floor 1326 angles from reservoir wall 1324 in a downward slope to drug dispensing opening 1322, which is formed by reservoir floor 1322.

First nebulization section 1312 includes a first reservoir channel 1328, a first valve 1330, a first barrier chamber 1332, a first barrier 1334, a first fluid chamber 1336, a first aerosol generator 1338, and a first aerosol region 1340. First reservoir channel 1328 is formed within housing 112 and runs from drug dispensing opening 1322 to first valve 1330. First valve 1330 is positioned outwardly from drug dispensing opening 1322 within housing 112, between first reservoir channel 1328 and first barrier channel 1332.

In some embodiments of the invention, first valve 1330 includes a first valve opening 1342, and a valve seal 1344. First valve opening 1342 is formed within housing 1112 as an outer opening of first reservoir channel 1328. First valve seal 1344 is disposed at first valve opening 1342 to selectively seal first valve opening 1342. First valve seal 1344, in one embodiment, may include a first float 1346 disposed within first valve 1330 at a first float reception cavity 1348. First float 1346 is composed of a material that enables first float 1346 to float in the drug solution, such as a closed cell foam. First float reception cavity 1348 is formed in housing 1112 between first reservoir channel 1328 and first barrier chamber 1332. First valve 1344 includes a first float/cavity interface 1350 that includes corresponding surfaces of first float 1346 and first float reception cavity 1348. First float 1346 is forced against first valve opening 1342 as first float 1346 rises to seal first valve opening 1342.

In the embodiment illustrated in FIG. 12, first float 1346 includes a first protruding center portion 1345 and first sloping lateral portions 1347. First protruding center portion 1345 protrudes from first sloping lateral portions 1347, which slope away from first protruding center portion 1345. First float reception cavity 1348 includes a first vertical channel 1349 and first lateral sloping surfaces 1351, arranged such that first protruding center portion 1345 is constantly positioned in first vertical channel 1349 even when first float 1346 is not sealing first valve opening 1342 to maintain the orientation of first float 1346. Maintaining the orientation of first float 1346 ensures that first sloping lateral portions 1347 will contact sloping lateral surfaces 1351 to seal first valve 1330 when first float rises due to its buoyancy.

According to an embodiment of the invention, first barrier chamber 1332, which communicates with first reservoir channel 1328 via first valve 1330, is formed within housing 1112 between first barrier 1334 and first aerosol region 1340. First barrier 1334 is mounted within housing 112 to a first mounting surface 1352 that is formed on an upper surface of first fluid chamber 1336, between first barrier channel 1332 and first fluid chamber 1336. First barrier forms a physical separation (i.e., a seal) between first barrier channel 1332 and first fluid chamber 1336. First barrier 1334 is composed of one or more materials designed to enable first barrier 1334 to be capable of transmitting ultrasonic energy therethrough, even under high temperature conditions. For example, polyetheretherketone (PEEK), or other materials may be used.

According to one embodiment of the invention, first fluid chamber 1336 is formed within housing 1112 between first barrier 1334 and first aerosol generator 1338. First fluid chamber 1336 holds a fluid 1339 in communication with first barrier 1334 and first acoustic wave aerosol generator 1338. Fluid 1339 includes one or more fluids capable of transmitting acoustic waves, such as, for example, water, or other fluids. Fluid 1339 may include one or more sterilant, such as, alcohol, or other sterilants.

In the embodiment of the invention illustrated in FIG. 12, first aerosol generator 1338 is disposed at a first aerosol generator seating portion 1354 formed within housing 112. In some instances, first aerosol generator 1338 includes a concave piezoelectric transducer with a silver electrode. First aerosol generator 1338 generates acoustic waves at a generator frequency, such as, for example, 2.5 MHz, or another frequency. The acoustic waves are focused at a focal point, or focal band, that is a focal length from first aerosol generator 1338. First aerosol generator seating portion 1354 is formed within housing 112 such that the focal point will be within first barrier chamber 1332. Other embodiments of first aerosol generator 1338 exist. First aerosol generator 1338 is operatively linked to control electronics 1316 so that control electronics 1316 can control various aspects of acoustic wave generation by first aerosol generator 1338, such as, for instance, activation and deactivation, or other aspects. First aerosol generator 1338 is operatively linked to power receiving connection 1130 so that power can be provided to first aerosol generator 1338 via this operative link.

According to an embodiment of the invention, first aerosol region 1340 includes a first fountain region 1356, one or more first aerosol region inlets 1358, a first chimney 1360, and a first drug return region 1362. First fountain region 1356 is formed within housing 1112 between first barrier chamber 1332 and first chimney 1360. First fountain region 1356 is open at a first end to first barrier chamber 1332 and at a second end to first chimney 1360. First fountain region 1356 is formed as a funnel with a smaller opening at the first end and a larger opening at the second end, or may be otherwise shaped.

The first aerosol region inlet 1358 is formed in housing 1112 at first fountain region 1356. First aerosol region inlet 1358 is in communication with inlet port 1132.

In one embodiment, first chimney 1360 is formed in housing 1112, and opens at a first end to first fountain region 1356. A first aerosol region ceiling 1374 is formed at a second end of first chimney 1360. First chimney 1360 provides operable communication between first fountain region 1356 and outlet 1116.

In some embodiments of the invention, first drug return region 1362 is formed in housing 1112. First drug return region 1362 is open at a first end to drug reservoir 1310. First drug return region 1362 communicates with first chimney 1360.

In accordance with an embodiment of the invention shown in FIG. 12, second nebulization section 1314 includes a second reservoir channel 1428, a second valve 1430, a second barrier chamber 1432, a second barrier 1434, a second fluid chamber 1436, a second aerosol generator 1438, and a second aerosol region 1440. Second reservoir channel 1428 is formed within housing 1112 and runs from drug dispensing opening 1422 to second valve 1430. Second valve 1430 is positioned outwardly from drug dispensing opening 1422 within housing 1112, between second reservoir channel 1428 and second barrier chamber 1432.

In the embodiment shown, second valve 1430 includes a second valve opening 1442, and a valve seal 1444. Second valve opening 1442 is formed within housing 1112 as an outer opening of second reservoir channel 1428. Second valve seal 1444 is disposed at second valve opening 1442 to selectively seal second valve opening 1442. In some instances, second valve seal 1444 includes a second float 1446, disposed within second valve 1430 at a second float reception cavity 1448. Second float 1446 is composed of materials that enable second float 1446 to float in the drug solution. Second float reception cavity 1448 is formed in housing 1112 between second reservoir channel 1428 and second barrier chamber 1432. Second valve 1444 includes a second float/cavity interface 1450 that includes corresponding surfaces of second float 1446 and second float reception cavity 1448, and is arranged to bias second float 1446 against second valve opening 1442 as second float 1446 rises to seal second valve opening 1442. For example, second float/cavity interface 1450 is structured similarly to first float/cavity interface 1350.

In other embodiments, valves 1330 and 1430 include, for example, one or more electrically operated solenoid valves that are actuated to open and/or close second valve 1430.

According to one embodiment of the invention, second barrier chamber 1432, which communicates with second reservoir channel 1428, via second valve 1430 is formed within housing 1112 between second barrier 1434 and second aerosol region 1440. Second barrier 1434 is mounted within housing 1112 to a second mounting surface 1452 that is formed on an upper surface of second fluid chamber 1436, between second barrier chamber 1432 and second fluid chamber 1436. Second barrier forms a physical separation (i.e., a seal) between second barrier chamber 1432 and second fluid chamber 1436. Second barrier 1434 is composed of one or more materials designed to enable second barrier 1434 to be capable of transmitting ultrasonic energy therethrough, even under high temperature conditions. For example, polyetheretherketone (PEEK), or other materials may be used.

The second fluid 1436 is formed within housing 1112 between second barrier 1434 and second aerosol generator 1438. Second fluid 1436 holds an fluid 1439 in communication with second barrier 1434 and second aerosol generator 1438. Fluid 1439 includes one or more fluids capable of transmitting acoustic waves, such as, for example, water, or other fluids. Fluid 1439 may include one or more sterilant, such as, alcohol, or other sterilants.

Second aerosol generator 1438 is disposed at a second aerosol generator seating portion 1454 formed within housing 1112. In one embodiment, second aerosol generator 1438 includes a concave piezoelectric transducer with a silver electrode. Second aerosol generator 1438 generates acoustic waves at a generator frequency, such as, for example, 2.5 MHz, or another frequency. The acoustic waves are focused at a focal point, or focal band, that is a focal length from second aerosol generator 1338. Second aerosol generator seating portion 1454 is formed within housing 1112 such that the focal point will be within second barrier chamber 1432. Second aerosol generator 1438 is operatively linked to control electronics 1316 so that control electronics 1316 can control various aspects of acoustic wave generation by second aerosol generator 1438, such as, for instance, activation and deactivation, or other aspects. Second aerosol generator 1438 is operatively linked to power connection 1130 so that power can be provided to second aerosol generator 1438 via this operative link.

Second aerosol region 1440 includes a second fountain region 1456, one or more second aerosol region inlets 1458, a second chimney 1460, and a second drug return region 1462.

Second fountain region 1456 is formed within housing 1112 between second barrier chamber 1432 and second chimney 1460. Second fountain region 1456 is open at a first end to second barrier chamber 1432 and at a second end to second chimney 1460. Second fountain region 1456 is formed as a funnel with a smaller opening at the first end and a larger opening at the second end, or may be otherwise shaped.

In some embodiments of the invention, second aerosol region inlet 1458 is formed in housing 1112 at second fountain region 1456. Second aerosol region inlet 1458 is in communication with inlet port 1132.

In the embodiment of FIG. 12, second chimney 1460 is formed in housing 1112, and opens at a first end to second fountain region 1456. A second aerosol region ceiling 1474 is formed at a second end of second chimney 1460. Second chimney 1460 provides operable communication between second fountain region 1456 and outlet 1116.

In one embodiment of the invention, second drug return region 1462 is formed in housing 1112. Second drug return region 1462 is open at a first end to drug reservoir 1310. Second drug return region 1462 communicates with second chimney 1460.

The barrier chambers 1332 and 1432 hold an amount of the drug solution at each of barriers 1334 and 1434. Nebulized particles of the drug solution are formed by the fountains and are delivered to aerosol regions 1340 and 1440. The fountains are formed by acoustic waves within the drug solution held in barrier chambers 1332 and 1432 at barriers 1334 and 1434. The acoustic waves are generated by aerosol generators 1338 and 1438. The acoustic waves transmitted from aerosol generators 1338 and 1438 to barrier chambers 1332 and 1432 via the fluid held in fluid chambers 1336 and 1436. The transmitted acoustic waves pass from fluid chambers 1336 and 1436 to barrier chambers 1332 and 1432 via barriers 1334 and 1434.

According to various embodiments of the invention, the acoustic waves transmitted to barrier chambers 1332 and 1432 are focused at the focal point. The drug solution in barrier chambers 1332 and 1432 absorbs the ultrasonic energy provided by the focused acoustic waves to create a fountain within each of barrier chambers 1332 and 1432. The ultrasonic energy delivered by the acoustic waves has a maximum density at or near the focal point of the acoustic waves. The fountains shed a portion of the drug solution as particles. Some of these particles are so large they immediately fall out. Some are small enough to pass into drug return regions 1362, 1462 before falling out. The remaining particles which are appropriately sized, pass out through first to second outlet 1116. In this manner, substantially consistent particle size is achieved.

In one embodiment of the invention, the nebulized particles are communicated from barrier chambers 1332 and 1432, through aerosol regions 1340 and 1440, and to the user via outlet 1116. More particularly, the nebulized particles and the larger droplets of the drug solution formed at the fountains are received by aerosol regions 1340 and 1440 at fluid chambers 1364 and 1464, and pass into chimneys 1360 and 1460. From chimneys 1360 and 1460, the nebulized particles are communicated to the user via outlet 1116. In contrast, due to size and/or weight, the larger droplets may not be communicated to the user, but instead may contact a surface of aerosol regions 1340 and 1440, such as aerosol region ceilings 1374 and 1474, or other surfaces. The larger droplets then condense on the contacted surface(s), thereby separating the larger droplets from the nebulized particles prior to delivery to the user. The drug solution contained in the condensed larger droplets are passed back to drug solution reservoir 1310 via drug return regions 1362 and 1462.

The nebulization of the drug solution by the fountains is enhanced when the focal point of the acoustic waves coincides (exactly or substantially) with an upper surface of the drug solution in first barrier chamber 1332. This requires a level of the upper surface to be controlled with some particularity to enhance the operation of the fountains. To maintain the level of the upper surface, an amount of the drug solution at barriers 334 and 434 is controlled by manipulating a flow of the drug solution from drug reservoir 1310 to barrier chambers 1332 and 1432 via reservoir channels 1328 and 1428 are controlled via valves 1330 and 1430 by independently sealing and unsealing valve openings 1342 and 1442 with valve seals 1344 and 1444. For example, when the level of the upper surface of the drug solution on either of barriers 1334 and/or 1434 reaches a threshold level at or near the focal point of the acoustic waves that corresponds to a threshold amount of the drug solution being present on one of barriers 1334 and 1434, corresponding one of floats 1346 and/or 1446 are positioned to seal valve openings 1342 and/or 1442 by virtue of the buoyancy of floats 1346 and 1446 with respect to the drug solution. However, as particles are formed by the fountains, the level of the upper surface in one or both of barrier chambers 1332 and 1432 may drop below the threshold level, which in turn lowers one or both of floats 1346 and 1446 from valve openings 1342 and 1442, thereby opening valves 1330 and/or 1430. This functionality is illustrated with respect to valves 330, and 430 in FIGS. 3, and 4.

Referring to FIG. 12, activation of aerosol generators 1338 and 1438 enable generation of particles of the drug solution to be propelled by the fountains into aerosol regions 1340 and 1440. As particles are propelled by the fountain into aerosol regions 1340 and 1440, the atmosphere within aerosol regions 1340 and 1440 is disturbed such that intake gas is pulled into particle receiving regions 1366 and 1466 via aerosol region inlets 1358 and 1458. Pulling air into particle receiving regions 1366 and 1466 may initiate the flow of intake gas through aerosol regions 1340 and 1440 to outlet 1116, which may in turn motivate the nebulized particles formed at the fountains toward outlet 1116. Thus, the atmospheric disturbances that may be caused by the nebulized particles from the fountains, and the resulting flow of intake gas through aerosol regions 1340 and 1440 may function in a cooperative manner to "drive" the delivery of nebulized particles from the fountains to the user without requiring additional active moving parts.

FIG. 13 is an exemplary cross sectional view of the handheld nebulizing device 1110, taken along cross section line 13-13, in accordance with another embodiment of the invention. In the embodiment illustrated in FIG. 13, device 1610 includes a first nebulization section 1612, a second nebulization section 1614, and control electronics 1616.

In the embodiment of FIG. 13, first nebulization section 1612 includes a first aerosol generator 1618, a first fluid 1620, a first barrier 1622, a first barrier chamber 1624, a first guide tube 1626, and a first separator structure 1628. First aerosol generator 1618 may include a concave piezoelectric transducer with a silver electrode. First aerosol generator 1618 generates acoustic waves at a generator frequency, such as, for example, 2.5 MHz, or another frequency. The acoustic waves are focused at a focal point that is a focal length from first aerosol generator 1618. Device 1110 is arranged such that the focal point is within first barrier chamber 1624. Other embodiments of aerosol generator 1618 exist. The inventors contemplate that various other aerosol generators could be employed with the teachings of the present invention. For instance, the aerosol generator may be a jet type nebulizer, a vibrating mesh nebulizer, a vibratory plate nebulizer, a traditional planar ultrasonic nebulizer, or an electrospray nebulizer.

According to one embodiment of the invention, first aerosol generator 1618 is seated in a first aerosol generator seating portion 1630 within intermediate module 1122. First aerosol generator seating portion 1630 is defined by an upper surface of a first seating portion wall 1632 that extends upward from a bottom plane of intermediate module 1122.

In this embodiment of the invention, first fluid 1620 is formed adjacent to aerosol generator seating portion 1630 such that first aerosol generator 1618 forms a portion of a lower surface of first fluid 1620.

A first barrier mounting surface 1634 is located at an upper surface of first fluid 1620. First barrier mounting surface 1634 defines a first barrier opening 1636. First barrier opening 1636 enable communication between first fluid 1620 and first barrier chamber 1624. First barrier 1622 is mounted to first barrier mounting surface 1634, effectively sealing first fluid 1620 from first barrier chamber 1624.

According to the embodiment illustrated in FIG. 13, first barrier chamber 1624 is formed by a first barrier chamber wall 1638 and a first barrier chamber floor 1640. First barrier chamber floor 1640 is sloped such that first barrier opening 1636 is a lowest point within first barrier chamber 1624.

In one embodiment of the invention, first guide tube 1626 is provided over first barrier 1622 such that a first end of first guide tube 1626 extends down into first barrier chamber 1624 and a second end of first guide tube 1626 extends out of first barrier chamber 1624. First guide tube 1626 is held in position over first barrier 1622 by a first guide tube collar 1638 associated with first separator structure 1628. First guide tube collar 1638 holds first guide tube 1626 in position such that the second end of first guide tube 1626 extends up into first separator structure 1628. First separator structure 1628 provides communication between the second end of first guide tube 1626 and outlet 1116.

According to an embodiment of the invention, first aerosol generator 1618 may be activated by control electronics 1616 to generate acoustic waves that are introduced into first fluid 1620. First fluid 1620 contains a fluid 1629 that is capable of transmitting the received acoustic waves. For example, the transmitting fluid 1629 may include water, or other fluids. In some instances, a sterilant, such as alcohol, or another sterilant, may be added to the transmitting fluid.

The second nebulization section 1614 includes a second aerosol generator 1718, a second fluid 1720, a second barrier 1722, a second barrier chamber 1724, a second guide tube 1726, and a second separator structure 1728. Second aerosol generator 1718 may include a concave piezoelectric transducer with a silver electrode. Second aerosol generator 1718 generates acoustic waves at a generator frequency, such as, for example, 2.5 MHz, or another frequency. The acoustic waves are focused at a focal point that is a focal length from second aerosol generator 1718. Device 1110 is arranged such that the focal point is within second barrier chamber 1724. Other embodiments of aerosol generator 1718 exist.

According to one embodiment of the invention, second aerosol generator 1718 is seated in a second aerosol generator seating portion 1630 within intermediate module 1122. Second aerosol generator seating portion 1630 is defined by an upper surface of a second seating portion wall 1632 that extends upward from a bottom plane of intermediate module 1122.

In the embodiment of the invention shown in FIG. 13, second fluid 1720 is formed adjacent to aerosol generator seating portion 1630 such that second aerosol generator 1718 forms a portion of a lower surface of second fluid 1720.

In this embodiment, a second barrier mounting surface 1634 is located at an upper surface of second fluid 1720. Second barrier mounting surface 1634 defines a second barrier opening 1636. Second barrier opening 1636 enable communication between second fluid 1720 and second barrier chamber 1724. Second barrier 1722 is mounted to second barrier mounting surface 1634, effectively sealing second fluid 1720 from second barrier chamber 1724.

The second barrier chamber 1724 is formed by a second barrier chamber wall 1638 and a second barrier chamber floor 1740. Second barrier chamber floor 1740 is sloped such that second barrier opening 1636 is a lowest point within second barrier chamber 1724.

In accordance with one embodiment of the invention, second guide tube 1726 is provided over second barrier 1722 such that a first end of second guide tube 1726 extends down into second barrier chamber 1724 and a second end of second guide tube 1726 extends out of second barrier chamber 1724. Second guide tube 1726 is held in position over second barrier 1722 by a second guide tube collar 1738 associated with second separator structure 1728. Second guide tube collar 1728 holds second guide tube 1726 in position such that the second end of second guide tube 1726 extends up into second separator structure 1728. Second separator structure 1728 provides communication between the second end of second guide tube 1726 and outlet 1116.

According to an embodiment of the invention, second acoustic wave aerosol generator 1718 may be activated by control electronics 1716 to generate acoustic waves that are introduced into second fluid 1720. Second fluid 1720 contains a fluid 1729 that is capable of transmitting the received acoustic waves. For example, the fluid 1729 may include water, or other fluids. In some instances, a sterilant, such as alcohol, or another sterilant, may be added to the transmitting fluid.

In one embodiment, the acoustic waves introduced to fluids 1620 and 1720 are transmitted from fluids 1620 and 1720 to barrier chambers 1624 and 1724 via barriers 1622 and 1722. The acoustic waves transmitted to barrier chambers 1624 and 1724 are focused at the focal points of aerosol generators 1618 and 1718. Pools of drug solution held within barrier chambers 1624 and 1724 absorb the ultrasonic energy provided by the focused acoustic waves, thereby energizing the drug solution to create a fountain at the top of guide tubes 1626, 1726. The fountains shed a portion of the drug solution as particles. Some of these particles are so large they immediately fall out. The remaining particles, which are appropriately sized, pass out of barrier chambers 1624, 1724. In this manner, a substantially consistent particle size is achieved.

In the embodiment of FIG. 13, the nebulization of the drug solution by the fountains is enhanced when the focal point of the acoustic waves coincides (exactly or substantially) with a surface of the drug solution in barrier chambers 1624 and 1724. This may require a level of the surface to be controlled with some particularity to enhance the operation of the fountain.

In the illustrated embodiment, the fountains are formed at the top of guide tubes 1626 and 1726. The drug solution within guide tubes 1626 and 1726 is propelled toward the second ends of guide tubes 1626 and 1726 by the ultrasonic energy from the acoustic waves. At the second ends of guide tubes 1626 and 1726, ultrasonic energy received by guide tubes 1626 and 1726 from the acoustic waves are transmitted to the drug solution propelled up from first ends of guide tubes 1626 and 1726, and is delivered to the drug solution at the second ends of guide tubes 1626 and 1726 to form the nebulized particles of the drug solution. Thus, guide tubes 1626 and 1726 enhance the formation of the nebulized particles of the drug solution within the fountains by energizing the drug solution within guide tubes 1626 and 1726 to nebulize drug solution that is not located at the respective focal points of the acoustic waves. Preferably the guide tubes are 2 mm-3 mm in diameter. One of ordinary skill in the art can best appreciate that the particles discharged from guide tubes 1626, 1726 can be adjusted by adjusting the size of the guide tubes 1626, 1726.

The above described systems are particularly well suited for delivering drugs to patients that have previously been difficult to administer. For instance, one such drug that has been difficult to deliver in an aerosolized form is pulmonary surfactants. Surfactants mainly consist of phosphelipids and surfactants proteins that are used to replace deficient endogenous surfactants in patient's lungs. There are a variety of surfactant medications available such as natural human surfactants (obtained from amniotic fluid or a bio-synthetic material), natural animal surfactants (obtained from bovine lung extracts, porcine lung extracts, or a bio-synthetic material), or synthetic preparations. What makes pulmonary surfactants particularly difficult to delivery in aerosol form is that they are highly viscous. Accordingly using one or more of the above described features of the present invention permits high speed delivery of viscous drugs such as pulmonary surfactants. Of course, the novel aspects of the present invention can also be used with a variety of other drug formulations.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A nebulizing device, comprising:
a housing including an outlet;
a drug reservoir for receiving a drug solution within the housing;
an aerosol generator in communication with a first portion of the drug solution;
wherein the aerosol generator forms nebulized particles from the portion of the drug solution to enable nebulized particles of the drug solution to be communicated to a user through the outlet;
a valve that permits drug solution within the reservoir to replenish a first portion of the drug solution when the first portion is less than a threshold amount, wherein the valve comprises a float that floats on a second portion of drug solution, the float substantially sealing the reservoir when the amount of the first portion of the drug solution is above the threshold amount, the float permitting drug solution to flow from the reservoir towards the aerosol generator when the amount of the first portion of the drug solution is less than the threshold amount.

2. A nebulizing device according to claim 1, comprising a separator structure that separates larger liquid droplets from smaller nebulized particles formed from the portion of drug solution by the aerosol generator.

3. A nebulizing device according to claim 2, wherein the larger liquid droplets in the separator structure are returned to the drug reservoir.

4. A nebulizing device, comprising:
a housing having an inlet and an outlet;
a plurality of chambers within the housing, the plurality of chambers being configured to hold separate portions of a drug solution, the plurality of chambers comprising:
a first chamber; and
a second chamber;
a plurality of acoustic wave generators, the plurality of acoustic wave generators comprising:
a first acoustic wave generator comprising a piezoelectric transducer having a concave shape, the first acoustic wave generator being in communication with the first chamber; and
a second acoustic wave generator comprising a piezoelectric transducer having a concave shape, the second acoustic wave generator being in communication with the second chamber;
the plurality of acoustic wave generators forming a corresponding plurality of fountains that generate nebulized particles of the drug solution, the plurality of fountains comprising:
a first fountain formed in the portion of the drug solution held in the first chamber by acoustic waves generated by the first acoustic wave generator; and
a second fountain formed in the portion of the drug solution held in the second chamber by acoustic waves generated by the second acoustic wave generator;
the plurality of fountains being in communication with the outlet to enable a user to inhale nebulized particles of the drug solution from the plurality of aerosol regions through the outlet.

5. A nebulizing drug device according to claim 4, wherein a plurality of barriers are provided, each barrier being functionally cooperative with a respective one of the aerosol generators.

6. A nebulizing device according to claim 5, wherein each barrier has an associated separate portion of fluid functionally cooperable therewith.

7. A nebulizing device according to claim 4, further comprising a drug solution reservoir in the housing that holds a portion of the drug solution within the housing, and a plurality of valves, each associated with one of the aerosol generator, and that opens to permit drug solution within the reservoir to be provided to the associated aerosol generator.

8. A nebulizing device, comprising:
a housing having an inlet and an outlet;
a plurality of aerosol generators in communication with a drug solution;
the plurality of aerosol generators forming a corresponding plurality of fountains that generate nebulized particles of the drug solution;
the plurality of fountains being in communication with the outlet to enable a user to inhale nebulized particles of the drug solution from the plurality of aerosol regions through the outlet;
a drug solution reservoir in the housing that holds a portion of the drug solution within the housing, and a plurality of valves, each associated with one of the aerosol generator, and that opens to permit drug solution within the reservoir to be provided to the associated aerosol generator wherein the valves open to provide the drug solution to the associated aerosol generator when an amount of solution is less than a threshold amount, and close to prevent fluid from the reservoir from being provided to the aerosol generator when the amount of drug solution is greater than the threshold amount.

9. A nebulizing device according to claim 8, wherein the valves each comprise a float.

10. A nebulizing device according to claim 4, further comprising a heater that heats the drug solution contained in a reservoir formed in the housing.

11. A nebulizing device according to claim 7, further comprising a heater that heats the drug solution in the reservoir.

12. A nebulizing device according to claim 4, wherein the heater heats the drug solution that is on the barrier.

13. A nebulizing device according to claim 10, further comprising a temperature sensor that determines a temperature of the drug solution in the reservoir, the temperature sensor being functionally connected with the heater to control operation of the heater and hence the temperature of the drug solution.

14. A nebulizing device according to claim 5, further comprising a plurality of guide tubes, each associated with one of the aerosol generators, having a first end in communication with the drug solution, and wherein the plurality of fountains are formed at the guide tubes such that a stream of drug solution that enters the first end of each of the guide tubes and exits a second end of the guide tube, wherein a majority of the nebulized particles are generated towards the second end of the fountain.

* * * * *